US011998487B2

(12) United States Patent
Katchinskiy et al.

(10) Patent No.: US 11,998,487 B2
(45) Date of Patent: Jun. 4, 2024

(54) OPTHALMOLOGICAL IMAGING AND LASER DELIVERY DEVICE, SYSTEM AND METHODS

(71) Applicant: PulseMedica Corp., Alberta (CA)

(72) Inventors: Nir Katchinskiy, Alberta (CA); Abdulhakem Elezzabi, Alberta (CA)

(73) Assignee: PulseMedica Corp., Alberta (CA)

( * ) Notice: Subject to any disclaimer, the term of this patent is extended or adjusted under 35 U.S.C. 154(b) by 0 days.

(21) Appl. No.: 18/475,558

(22) Filed: Sep. 27, 2023

(65) Prior Publication Data

US 2024/0016660 A1    Jan. 18, 2024

Related U.S. Application Data

(63) Continuation of application No. 18/248,653, filed as application No. PCT/CA2021/051451 on Oct. 15, 2021.

(30) Foreign Application Priority Data

Oct. 16, 2020    (CA) .................................. CA 3096285

(51) Int. Cl.
    *A61F 9/008*    (2006.01)
    *A61B 18/20*    (2006.01)
    *A61B 34/00*    (2016.01)

(52) U.S. Cl.
    CPC .............. *A61F 9/008* (2013.01); *A61B 34/25* (2016.02); *A61B 2018/2025* (2013.01); *A61B 2018/208* (2013.01); *A61F 2009/00846* (2013.01); *A61F 2009/00851* (2013.01); *A61F 2009/00897* (2013.01)

(58) Field of Classification Search
    CPC ............ A61F 9/008; A61F 2009/00846; A61F 2009/00851; A61F 2009/00897; A61B 34/25; A61B 2018/2025; A61B 2018/208
    See application file for complete search history.

(56) References Cited

U.S. PATENT DOCUMENTS

| 7,980,696 B1 * | 7/2011 | Taki ........................ A61B 3/102 351/205 |
| 10,117,576 B2 * | 11/2018 | de Boer ................. A61B 3/102 |
| 10,694,939 B2 * | 6/2020 | Kuo ....................... A61B 3/1233 |

(Continued)

FOREIGN PATENT DOCUMENTS

| CN | 109938919 A * | 6/2019 | ............. A61F 9/008 |
| CN | 109938919 A | 6/2019 | |

(Continued)

OTHER PUBLICATIONS

International Search Report for International Application No. PCT/CA2021/051451, mailed Dec. 20, 2021, 4 pages.

*Primary Examiner* — Carl H Layno
*Assistant Examiner* — Manolis Pahakis
(74) *Attorney, Agent, or Firm* — Perkins Coie LLP

(57) ABSTRACT

An ophthalmological device and system is described that allows the simultaneous imaging of an eye using both scanning laser ophthalmoscopy (SLO) and optical coherence tomography (OCT). Further the device and system is capable of targeting and delivering a femtosecond treatment laser for treatment of an eye condition. The system further includes a machine learning algorithm to provide a suggested treatment procedure.

21 Claims, 14 Drawing Sheets

(56) References Cited

U.S. PATENT DOCUMENTS

| | | | |
|---|---|---|---|
| 2007/0046948 A1* | 3/2007 | Podoleanu | A61B 3/14 356/497 |
| 2007/0115481 A1* | 5/2007 | Toth | A61B 3/0025 356/497 |
| 2009/0093798 A1* | 4/2009 | Charles | A61B 3/135 606/4 |
| 2010/0094135 A1* | 4/2010 | Fang-Yen | G01B 9/02057 351/205 |
| 2010/0182610 A1* | 7/2010 | Utsunomiya | G01B 9/02068 356/498 |
| 2010/0290007 A1* | 11/2010 | Van de Velde | G01B 9/0203 351/221 |
| 2011/0043661 A1* | 2/2011 | Podoleanu | G01B 9/02069 348/370 |
| 2011/0058175 A1* | 3/2011 | Suehira | A61B 5/0073 356/450 |
| 2011/0134436 A1* | 6/2011 | Podoleanu | G01B 9/02004 356/512 |
| 2011/0234978 A1* | 9/2011 | Hammer | A61B 3/1015 351/208 |
| 2012/0002164 A1* | 1/2012 | Yamamoto | A61B 3/1025 351/206 |
| 2012/0154747 A1* | 6/2012 | Makihira | A61B 3/113 351/246 |
| 2012/0165799 A1* | 6/2012 | Yamamoto | A61F 9/00821 606/4 |
| 2012/0274904 A1* | 11/2012 | Saito | A61B 3/12 351/221 |
| 2012/0294500 A1* | 11/2012 | Utsunomiya | A61B 3/102 382/128 |
| 2013/0286348 A1* | 10/2013 | Makihira | A61B 3/1025 351/246 |
| 2014/0104618 A1* | 4/2014 | Potsaid | G02B 27/0068 356/497 |
| 2015/0116664 A1* | 4/2015 | Uchida | A61B 3/1025 351/246 |
| 2015/0141972 A1* | 5/2015 | Woodley | A61F 9/00827 606/5 |
| 2016/0074221 A1* | 3/2016 | Tassignon | G06F 16/24 606/4 |
| 2016/0250067 A1* | 9/2016 | Iwata | A61F 9/008 606/4 |
| 2016/0284103 A1* | 9/2016 | Huang | G01B 9/02091 |
| 2017/0007112 A1* | 1/2017 | Gonzalez | A61F 9/0084 |
| 2017/0035291 A1* | 2/2017 | Jiao | A61B 3/14 |
| 2017/0189228 A1* | 7/2017 | Yang | A61F 9/00802 |
| 2018/0116502 A1* | 5/2018 | Ishinabe | A61B 3/117 |
| 2018/0200112 A1* | 7/2018 | Krampert | A61B 3/1005 |
| 2018/0271362 A1* | 9/2018 | Palczewski | A61B 3/06 |
| 2018/0344150 A1* | 12/2018 | Bajraszewski | G01B 9/02091 |
| 2018/0353064 A1 | 12/2018 | Soetikno et al. | |
| 2019/0000316 A1* | 1/2019 | Hirose | A61B 3/1025 |
| 2019/0125178 A1* | 5/2019 | Murata | A61B 3/1225 |
| 2019/0278972 A1* | 9/2019 | Anderson | A61B 3/145 |
| 2019/0339356 A1* | 11/2019 | Schildknecht | G01B 11/026 |
| 2020/0015675 A1* | 1/2020 | Shibutani | A61B 3/102 |
| 2020/0242768 A1* | 7/2020 | Ashok | A61B 3/154 |
| 2020/0288973 A1* | 9/2020 | Ono | A61B 3/0025 |
| 2021/0045672 A1* | 2/2021 | Jia | G16H 50/50 |
| 2021/0202062 A1* | 7/2021 | Gray | G06N 3/08 |
| 2022/0117780 A1* | 4/2022 | Zhang | A61B 3/13 |
| 2022/0151483 A1* | 5/2022 | Ono | A61B 5/7267 |
| 2022/0390369 A1* | 12/2022 | Piestun | G01N 21/47 |
| 2023/0372153 A1* | 11/2023 | Katchinskiy | A61F 9/008 |
| 2024/0016660 A1* | 1/2024 | Katchinskiy | A61F 9/008 |

FOREIGN PATENT DOCUMENTS

| | | |
|---|---|---|
| JP | 2015195923 A | 11/2015 |
| JP | 2017184874 A | 10/2017 |
| WO | 2020/012841 A1 | 1/2020 |

* cited by examiner

OPTHALMOLOGICAL IMAGING AND LASER DELIVERY DEVICE, SYSTEM AND METHODS

RELATED APPLICATION

The current application is a continuation of U.S. application Ser. No. 18/248,653 filed Apr. 11, 2023, which claims priority to PCT International Application No. PCT/CA2021/051451 filed Oct. 15, 2021, which applications claim priority to Canadian Application No. 3,096,285 filed Oct. 16, 2020, which is hereby incorporated by reference in its entirety.

TECHNICAL FIELD

The current application relates to ophthalmological devices, systems and methods and in particular to devices, systems and methods for imaging and laser treatment of an eye.

BACKGROUND

Imaging of an eye is important for identifying conditions of the eye. Various imaging techniques may be used for capturing images of the interior compartments of the eye. For example, scanning laser ophthalmoscopy (SLO) imaging may provide a 2-dimensional image of a portion of the eye, such as the retina or of cornea. Optical coherence tomography (OCT) imaging may provide 3-dimensional and/or cross-section images of a portion of the retina or cornea. Other imaging techniques may be used for capturing an image of at least a portion of the fundus of the eye.

Imaging of the eye may be used for identifying eye conditions requiring treatment. Treatment of eye conditions may be performed using lasers, with the specific targeting location of the laser beam or pulse determined from the captured images.

An additional, new and/or improved ophthalmological device capable of imaging and treating one or more eye conditions is desirable.

SUMMARY

In accordance with the present disclosure there is provided an imaging and laser delivery device for treatment of an eye condition, the device comprising: a scanning laser ophthalmoscopy (SLO) optical pathway for SLO imaging; an optical coherence tomography (OCT) optical pathway for OCT imaging, a treatment optical pathway for a treatment laser; and a delivery optical pathway comprising an objective lens that focuses light from the SLO optical pathway, the OCT optical pathway and the treatment optical pathway onto a portion of an eye being treated for the eye condition.

In a further embodiment of the imaging and laser delivery device, the imaging and laser delivery device further comprises a device controller for: controlling operation of components of the SLO optical pathway, the OCT optical pathway and the treatment optical pathway; and providing an interface between the imaging and laser delivery device and a computing device.

In a further embodiment of the imaging and laser delivery device, the imaging and laser delivery device further comprises: an SLO light source or SLO light source port for coupling the laser delivery device to an external SLO light source; an OCT light source or OCT light source port for coupling the laser delivery device to an external OCT light source; and a treatment light source or treatment light source port for coupling the laser delivery device to an external treatment light source.

In a further embodiment of the imaging and laser delivery device: the SLO light source or external SLO light source operate at an SLO wavelength; the OCT light source or external OCT light source operate at an OCT wavelength; the treatment light source or external treatment light source operate at a treatment wavelength, and wherein each of the SLO wavelength, OCT wavelength and treatment wavelength are different wavelengths.

In a further embodiment of the imaging and laser delivery device the delivery optical pathway comprises one or more optical devices for separating returning light from the eye through the objective lens and delivering a portion of the returning light to one of the SLO optical pathway or the OCT optical pathway based on a wavelength of the portion of the returning light.

In a further embodiment of the imaging and laser delivery device the SLO optical pathway comprises: XY scanning optics for scanning an SLO beam across a portion of the eye; an SLO detector for detecting light from the SLO beam returning from the eye through a portion of the SLO optical pathway.

In a further embodiment of the imaging and laser delivery device the XY scanning optics comprise one or more of: a galvonmeter; a resonant scanner; a non-resonant scanner a spinning mirror: and a spinning prism.

In a further embodiment of the imaging and laser delivery device the OCT optical pathway comprises: an optical splitter/combiner coupled to an OCT light source and an OCT detector; a sample optical pathway optically coupling the optical splitter/combiner to the delivery pathway; and a reference optical pathway optically coupling the optical splitter/combiner to a return mirror, wherein light returning from the sample optical pathway and the reference optical pathway are combined in the optical splitter/combiner before being detected by the OCT detector.

In a further embodiment of the imaging and laser delivery device a position of the return mirror is adjustable in order to lengthen or shorten a length of the reference pathway.

In a further embodiment of the imaging and laser delivery device the reference pathway comprises an adjustable thickness material to compensate for dispersion within the eye.

In a further embodiment of the imaging and laser delivery device the treatment optical pathway comprises at least one of adaptive optics, prism pair, grating pair, dielectric mirror coatings, and optical fiber for pre-compensating a treatment laser pulse based on the thickness of the adjustable thickness material in the reference pathway of the OCT optical pathway.

In a further embodiment of the imaging and laser delivery device, the imaging and laser delivery device further comprises: a second therapeutic laser.

In a further embodiment of the imaging and laser delivery device, the imaging and laser delivery device further comprises: an alignment system for aligning the therapeutic laser to the OCT optical pathway.

In a further embodiment of the imaging and laser delivery device, the alignment system comprise a coarse alignment section and a fine alignment section.

In a further embodiment of the imaging and laser delivery device, the coarse alignment section comprise a pair of CMOS sensors arranged at respective ends of different length optical paths of a coarse alignment beam split from the therapeutic laser.

In a further embodiment of the imaging and laser delivery device, the coarse alignment beam is split from the therapeutic laser before injection into the OCT pathway.

In a further embodiment of the imaging and laser delivery device, the fine alignment section comprises a pair of quadrature photodiodes (QPD) arranged at respective ends of different length optical paths of a fine alignment beam split from the therapeutic laser.

In a further embodiment of the imaging and laser delivery device, the alignment system comprises positioning optics for controllably adjusting the alignment of the therapeutic laser.

In a further embodiment of the imaging and laser delivery device, the alignment system uses a positive reinforcement learning algorithm to control the positioning optics independent of optical geometry.

In a further embodiment of the imaging and laser delivery device, the imaging and laser delivery device further comprises a pilot laser passing through at least a portion of the treatment optical pathway.

In a further embodiment of the imaging and laser delivery device, the pilot laser has a pilot wavelength that can be detected by at least one of the SLO detector and the OCT detector.

In a further embodiment of the imaging and laser delivery device, the pilot laser is used to align the treatment laser with at least one of the SLO imaging and the OCT imaging.

In a further embodiment of the imaging and laser delivery device, the imaging and laser delivery device further comprises a beam splitter for directing a portion of the pilot laser returning from the eye to a pilot sensor for detecting the pilot laser, wherein the pilot sensor is used to generate an image of the eye that can be registered to an SLO image.

In a further embodiment of the imaging and laser delivery device, the imaging and laser delivery device further comprises a beam splitter for directing a portion of the treatment laser returning from the eye to a treatment sensor for detecting the treatment laser, wherein the treatment sensor is used to generate an image of the eye that can be registered to an SLO image.

In a further embodiment of the imaging and laser delivery device, the treatment laser is a femtosecond laser.

In accordance with the present disclosure there is provided further provided a laser imaging and delivery system for treatment of an eye condition comprising: an imaging and laser delivery device as described above; and a computing device for controlling operation of the imaging and laser delivery device and providing a graphical user interface to a user of the imaging and laser delivery system.

In a further embodiment of the imaging and laser delivery system, the computing device is configured to: capture SLO images and OCT images; register the captured SLO images and OCT images to planning images of a treatment plan for treating the eye condition; and controlling the treatment laser according to the treatment plan.

In a further embodiment of the imaging and laser delivery system, the computing device is further configured to: track eye movement using the captured SLO images; and control the treatment laser according to the treatment plan and the tracked eye movement.

In a further embodiment of the imaging and laser delivery system, the computing device is further configured to: identify unsafe regions for laser treatment within the eye; and stop the treatment laser if treatment will occur within the unsafe regions.

In a further embodiment of the imaging and laser delivery system, the computing device is further configured to: generate a graphical user interface (GUI) displaying the SLO images and OCT images.

In a further embodiment of the imaging and laser delivery system, the GUI is used to generate the treatment plan.

In a further embodiment of the imaging and laser delivery system, the GUI displays progress of a treatment plan during treatment.

In accordance with the present disclosure there is provided a use of the imaging a laser delivery system as described above in the treatment of one or more eye conditions comprising diabetic retinopathy, age-related macular degeneration, vitreomacular traction, tears, detachments and holes, glaucoma, and vein occlusion.

BRIEF DESCRIPTION OF THE DRAWINGS

Further features and advantages of the present disclosure will become apparent from the following detailed description, taken in combination with the appended drawings, in which.

DETAILED DESCRIPTION

An imaging and laser treatment system is described that includes both a scanning laser ophthalmoscopy (SLO) imaging device, and an optical coherence tomography (OCT) imaging device for imaging the eye, which may be done simultaneously using both devices. Additionally, the imaging and laser delivery system includes a treatment laser that can be used for carrying out treatment of an ocular condition. The treatment laser may be a therapeutic laser or surgical laser. The SLO imaging, OCT imaging, and therapeutic laser may pass through a common objective lens for delivery to the eye being imaged and/or treated. Further, the SLO imaging device, or more particularly the images from the SLO imaging device, may be used to identify eye movement and account for the eye movement in the OCT imaging device and/or the targeting of the therapeutic laser. The combination of the SLO imaging, OCT imaging, and therapeutic laser can provide a system that allows for both planning and performing a treatment of an ocular condition using a single system. While the planning and treatment may be performed at separate times, which may require the individual to return one or more times, the planning and treatment may also be performed at a single time. It will be appreciated that additional components may be included in the imaging and laser treatment system, including for example fundus imaging components, a pilot laser system, additional treatment lasers, etc.

Figure 1:
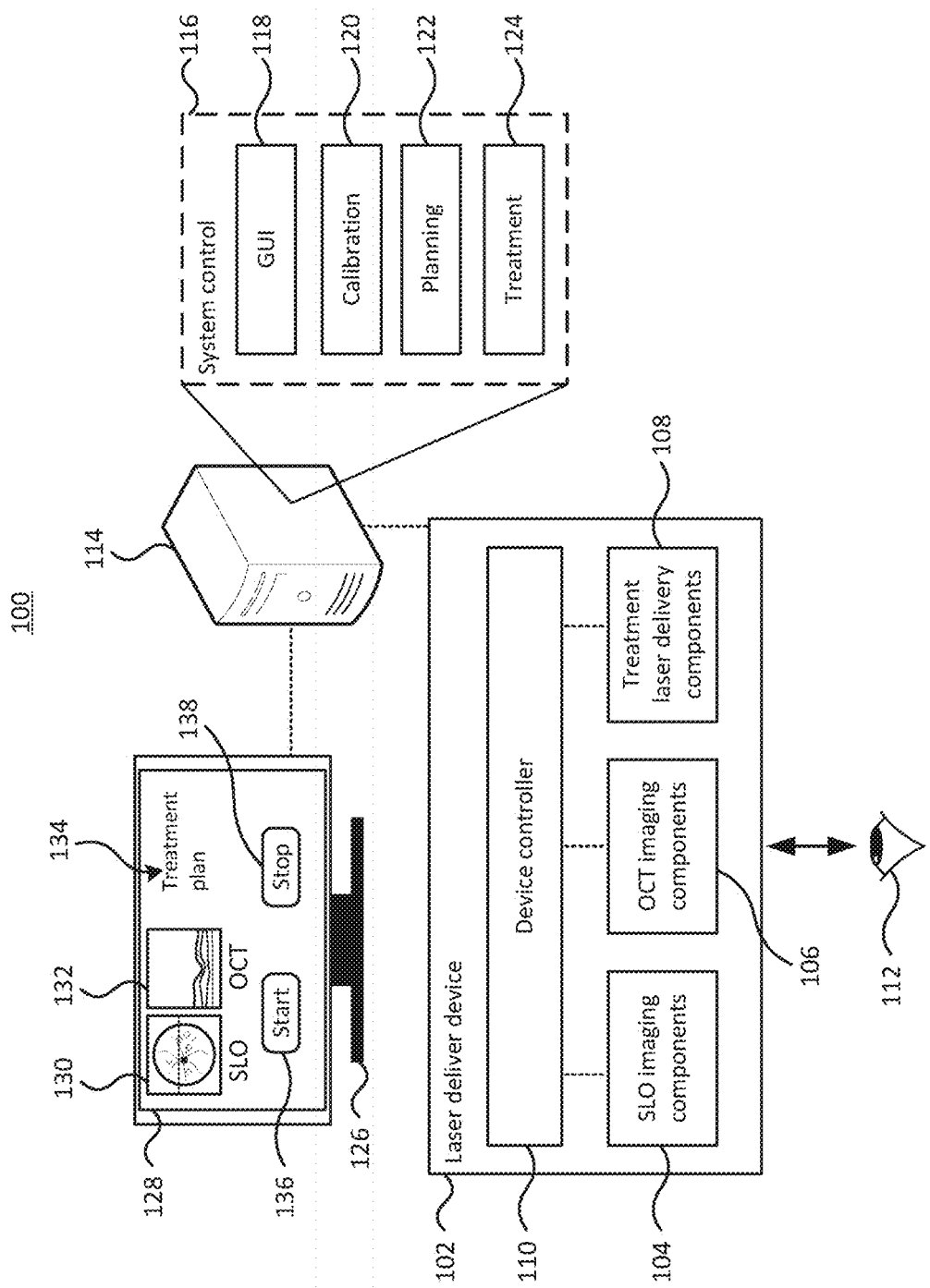
FIG. 1 depicts components of an ocular imaging and laser treatment system.

FIG. 1 depicts components of an ocular imaging and laser treatment system. The system 100 comprises an imaging and laser delivery device 102. The device 102 comprises SLO imaging components 104, OCT imaging components 106 and treatment laser delivery components 108. The imaging and laser delivery components may be controlled by a device controller 110. The light for the SLO imaging. OCT imaging and treatment laser may be delivered to an eye 112, or possibly other target, being imaged and/or treated. The imaging light for SLO and OCT imaging is reflected back to the respective detectors.

The device controller 110 may provide an interface between the device 102 and a computing device 114. The computing device 114 provides various system control functionality 116 for operating the imaging and laser delivery device 102. While the computing device 114 is depicted as a separate computing device 114, it is possible to incorporate the computing device 114 into the imaging and laser delivery device 102. The device controller 110 may capture signals from respective detectors/camera of the SLO, and OCT imaging components 104, 106 as well as controlling other components, such as the sources of the imaging components, 104, 106, and treatment laser delivery components 108, focusing components, or other components.

The computing device 114 may comprise one or more processing units (not depicted) for executing instructions, one or more memory units (not depicted) storing data and instructions, which when executed by the one or more processing units configure the computing device to provide the system control functionality 116. The system control functionality 116 may include graphical user interface (GUI) functionality 118 that provides a GUI for operating the imaging and laser delivery device. Calibration functionality 120 may be provided in order to calibrate the imaging and laser delivery device 102 and in particular to align and correlate the SLO imaging components 104, OCT imaging components 106 and the treatment laser delivery components 108 so that locations in the SLO images and OCT images can be precisely aligned with each other and be accurately targeted by treatment laser. Planning functionality 122 may be provided that allows a treatment plan to be developed for treating a particular ocular condition. The planning functionality 122 may use the GUI functionality to allow a user to define the treatment plan. Additionally or alternatively, the planning functionality may incorporate automated, or semi-automated, planning functionality that may identify laser treatment locations within the captured images. Treatment functionality 124 may control the components of the device 102, including the treatment laser delivery components 108, in order to carry out the treatment plan in order to treat, or at least partially treat, an ocular condition.

The GUI functionality 118 may present the generated GUI on a display 126. Although depicted as a separate display, the display could be incorporated into the imaging and laser delivery device 102. Although the GUI presented may vary depending upon what information needs to be, or may be desirable to be, displayed to the user. FIG. 1 depicts a GUI 129 that could be displayed during treatment. For example, the GUI may display a SLO image 130, and an OCT image 132. The SLO image may include an indication of the location of the cross section of the OCT image. The SLO image, and the OCT image may include indications of treatment locations that have not yet been treated as well as treatment locations that have been treated. The GUI 134 may include other details of the treatment plan that may be relevant to the user as well as graphical elements for starting 136, and stopping 138 the treatment.

The device 102 and system 100 depicted in FIG. 1 broadly comprise the optical hardware, control electronics and software. The components are described in further detail below. The system 100 may be used for imaging eyes to identify areas for treatment and carrying out the treatment. The treatment may be for a wide range of different ocular conditions including, for example, age-related macular degeneration (AMD), vitreomacular traction syndrome (VTS), diabetic retinopathy, cataracts, choroidal neovascularization, microaneurysm, glaucoma, epiretinal membrane (ERM), retinal tears and detachment, central or branch vein occlusion.

Figure 2:
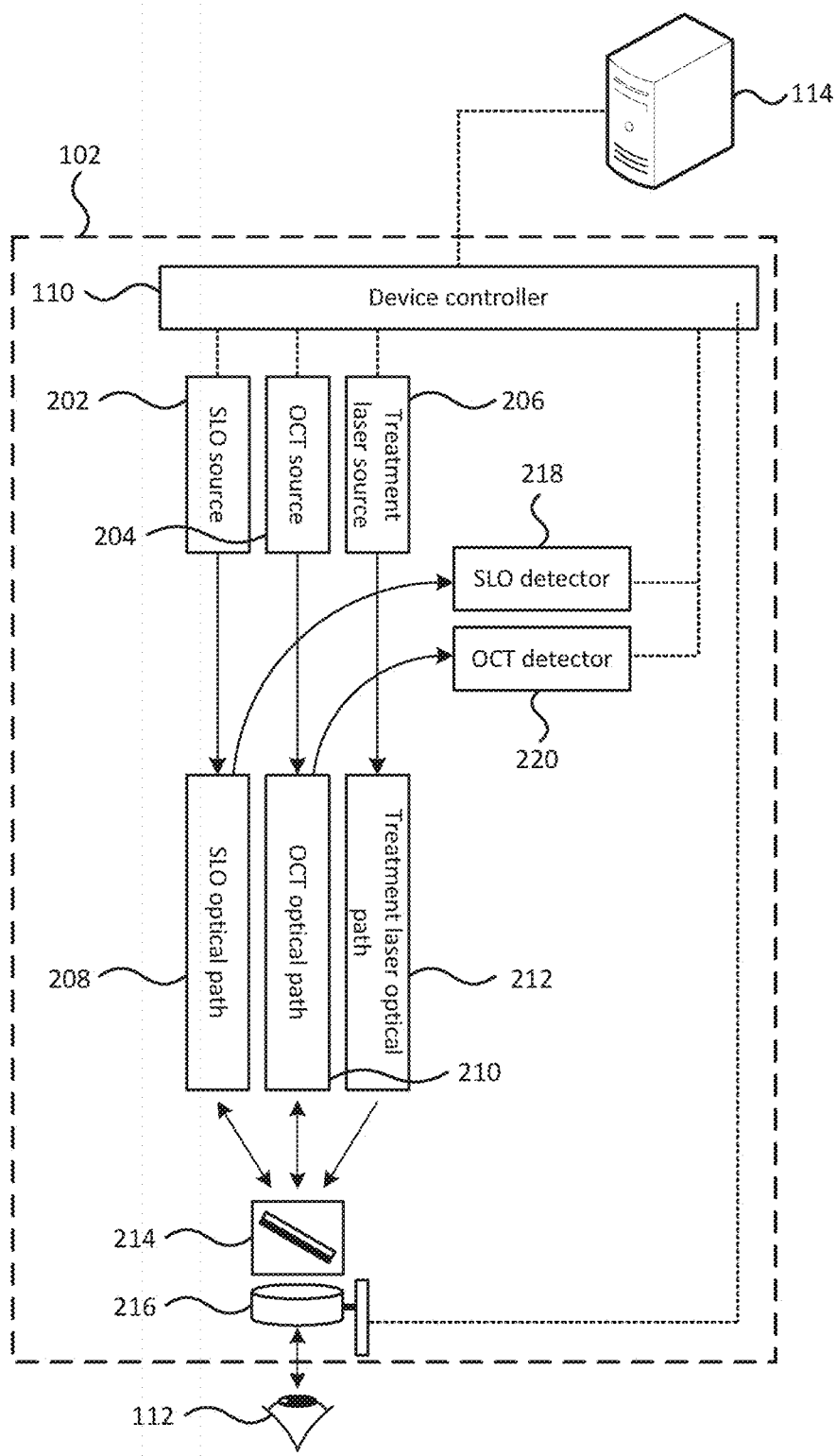
FIG. 2 depicts optical paths of an imaging and laser treatment system.

FIG. 2 depicts optical paths of an imaging and laser delivery system. As depicted, the imaging and laser delivery device 102 comprises a SLO source 202. The SLO source 202 may be for example a diode laser, gas laser, dye laser, solid-state laser, continuous wave laser, pulsed laser, ultrashort laser pulses, super radiant diode light source, non-linearly generated light from nonlinear optical material (e.g. supercontinuum light, harmonic generation light, sum or difference frequency generated light) or a port for coupling the device 102 to the laser. The SLO laser may operate at a range of different wavelengths, including for example between 100 nm-3000 nm. The OCT source 204 may comprise a low-coherence light source suitable for use in OCT imaging such as for example a superluminesccent diode, ultrashort laser pulses, super radiant diode light source, non-linearly generated light from nonlinear optical material (e.g. supercontinuum light, harmonic generation light, sum or difference frequency generated light), or a port for coupling the device 102 to the superluminesccent diode. The treatment laser source 206 may comprise a treatment laser or a port for coupling the device 102 to the treatment laser. The treatment laser may be for example a gas laser, fiver laser, dye laser, a fiber or free-space femtosecond/picosecond/nanosecond laser, a solid-state laser (pulsed or continuous wavelength), a pulsed or continuous wavelength diode laser, an optical parametric oscillator, an optical amplifier optical, and optical parametric amplifier, or a coherent light generated form nonlinear optical processes (e.g. sum, difference, and second harmonic light generation) etc. The device controller 110 may provide control signals to the light sources in order to control them including for example, turning the lasers/lights on and off as well as possibly adjusting controllable parameters.

Each of the sources 202, 204, 206 is coupled to respective optical paths 208, 210, 212 that direct the light from the sources to the target 112. Each of the optical paths may have various optical elements including lenses, beam splitters, combiners, mirrors, filters polarizers, adaptive optics, prisms, gratings, optical fibers, etc. The light from the sources may pass through a beam splitter/combiner 214 that combines and directs light output from each of sources to the eye 112 through one or more telescope lenses 216 that focus the light on the eye. A contact lens or a combination of contact lenses may be used on the eye in order to better couple the light from the telescope lenses to the eye.

Light from the treatment laser can be used for imaging of the eye, however, the treatment light returning from the eye does not need to be directed to a detector. In contrast, the light from the SLO, and OCT sources reflects of portions of the eye being imaged and the reflected light may be split by the beam splitter 214 and directed back to the respective optical paths 208, 210. The returning light may be split based on for example the wavelengths used for SLO, and OCT imaging, or if the same or similar wavelengths are used and as such splitting the returning light based on the wavelength is impossible, or difficult, the beam may be split based on polarization if the SLO and OCT light have different polarization states.

The optical elements of both the SLO and OCT optical paths direct the light from the source to the target 112, and for the SLO imaging and OCT imaging direct returning light of each source to a SLO detector 218 and OCT detector 220 respectively. Each of the optical paths 208, 210, 212 are described in further detail below with regard to FIGS. 3 to 5. Additional optical systems, not depicted in FIG. 2, may be included in the imaging and treatment system. For example, one or more fundus cameras may be incorporated for imaging the eye, one or more pilot laser systems, additional treatment laser systems, etc.

Figure 3:
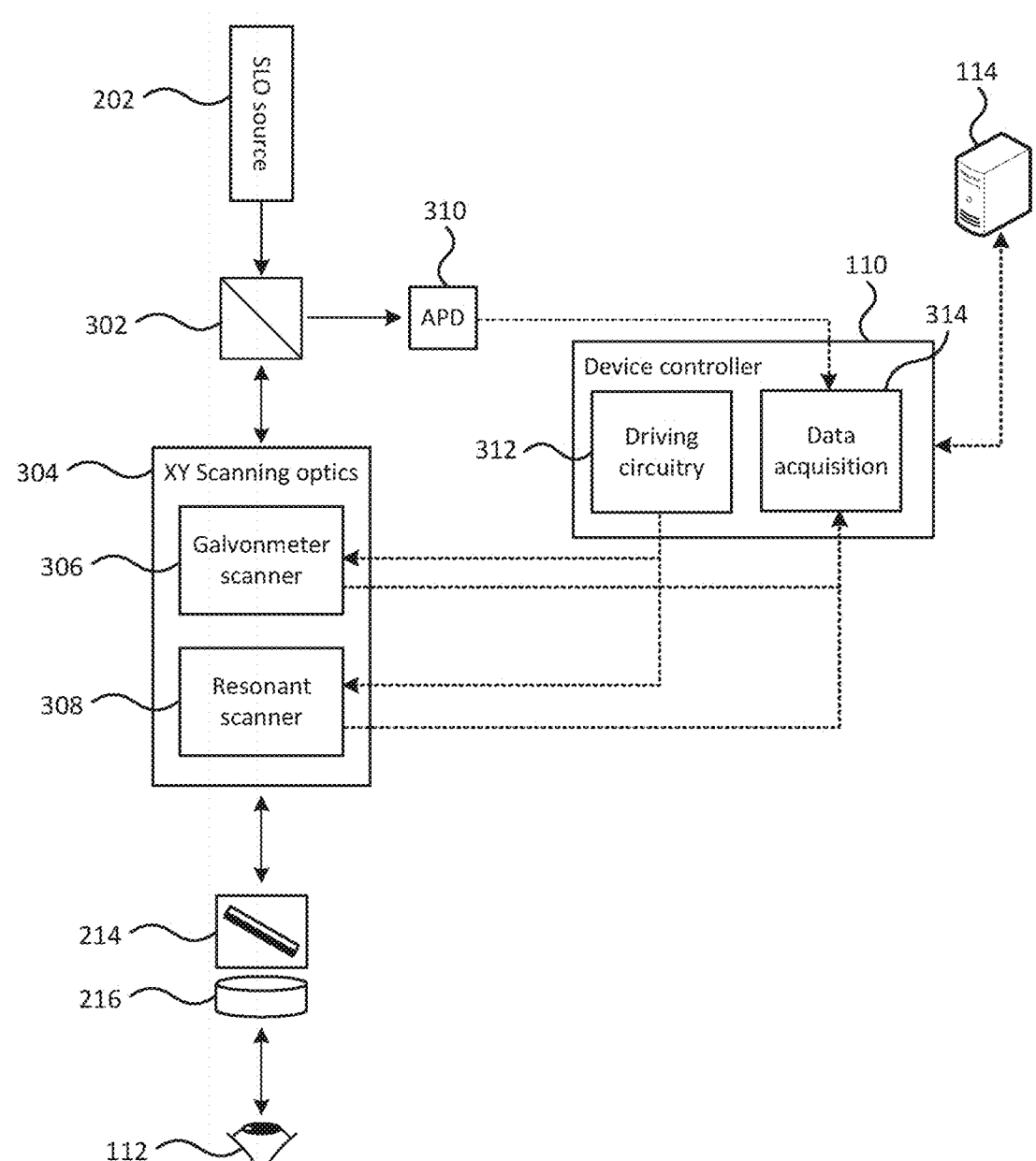
FIG. 3 depicts components of an SLO imaging portion of the imaging and laser treatment system.

FIG. 3 depicts components of an SLO imaging portion of the imaging and laser treatment system. The SLO source 202 outputs light useful for SLO imaging. The SLO optical path may comprise free-space optical elements that are arranged to deliver the light from the source 202 to the eye 112 and direct the returning light from the eye to the SLO detector. The SLO optical path includes a beam splitter, or other optical device, such as an optical circulator or a directional coupler, 302 capable of directing light from the source 202 to the eye 112 through scanning optics 304, the beam splitter 214 and the telescope optics 216, which may comprise one or more lenses, filters, apertures, etc. The telescope optics 216 may include one or more lenses capable of moving along a Z-axis, which beings the lenses away from or towards the eye. Moving the optics along the Z-axis can change the focus to different parts of the eye such as the cornea or the retina or anywhere inside the eye's internal compartments. The scanning optics 304 comprise optical devices capable of scanning the light across the eye. As depicted, the devices may include a galvanometer, or galvo, 306 that can scan the light through a first axis, such as the Y-axis, as well as a resonant scanner 308 that scans the light through a second orthogonal axis, such as the X-axis. Although described as using a combination of a galvo and a resonant scanner, it is possible to use other devices to scan along either the X or Y axis. For example the scanning optics could be provided by an acousto-optic deflector, an electro-optic deflector, a non-resonant scanner, spinning mirrors, spinning prisms, micro electro-mechanical (MEM) mirrors. Further, rather than using two scanning devices it is possible to use a single optical scanning device capable of controllably scanning the optical beam in both the X and Y axis such as a 2D MEMs mirror. The resonant scanner 308 is capable of providing a high scanning rate as it operates at a significantly higher rate than the galvo. For example, in order to generate a 512×512 raster image of the eye, the resonant scanner will need to direct the light to 512 locations each time the galvo moves to a new row position. It is possible that the XY-scanning optics 304 use two galvos, although the imaging rate may be reduced. Other devices, such as micro mirror devices, may be used for scanning the light across the eye in a raster pattern. The XY-scanning optics 304 may be driven by driving circuitry 312 in the device controller 110. Signals from the resonant scanner may be captured by a data acquisition circuitry 314 which may be used to synchronize movement of the galvo with that of the resonant scanner so that a new row is moved to when a scan of a column is completed by the resonant scanner.

Reflected light from the eye returns through the same optical path to the beam splitter 302, which splits the returning light from the light of the source and directs the returning light to the SLO detector, which is depicted as an avalanche photodetector (APD) 310. The APD signal may be captured by the data acquisition circuitry 314. Although depicted as an APD, other detectors are possible, including for example a tube photomultiplier of a photodiode with an amplifier or a semiconductor-based photo multiplier or a charged coupled device, or a camera. The data acquisition circuitry may operate substantial as an electronic device that can measure the voltage/current of relevant signals at a high enough frequency to properly measure the signals. The device controller may provide an interface that may be used to provide the captured data, including the imaging data, to the computer 114 as well as receive control information for controlling the SLO source and scanning optics from the computer 114.

The optical path may include additional components including, for example one or more lenses, mirrors, gratings, etc. for focusing and/or directing light, one or more filters, apertures, etc. The additional components may provide additional functionality such as wavefront aberration detection and correction or compensation, intensity detection and correction or compensation.

The above has described using a single SLO source of a Additionally, for example, the SLO source may have multiple individual light sources, such as a red, green and blue source that are combined into a single beam. Using combined red, green and blue light sources, and corresponding detectors, allows true colour SLO images to be captured. Additionally or alternatively, it is possible to use a femtosecond laser as the SLO source, it may be possible to provide real time flourescin angiography. Further still, although not depicted in FIG. 3 it is possible for the optical source, or the optical path, may include adaptive optics that can significantly improve imaging resolution allowing the visualization of, for example, single cells.

Figure 4:
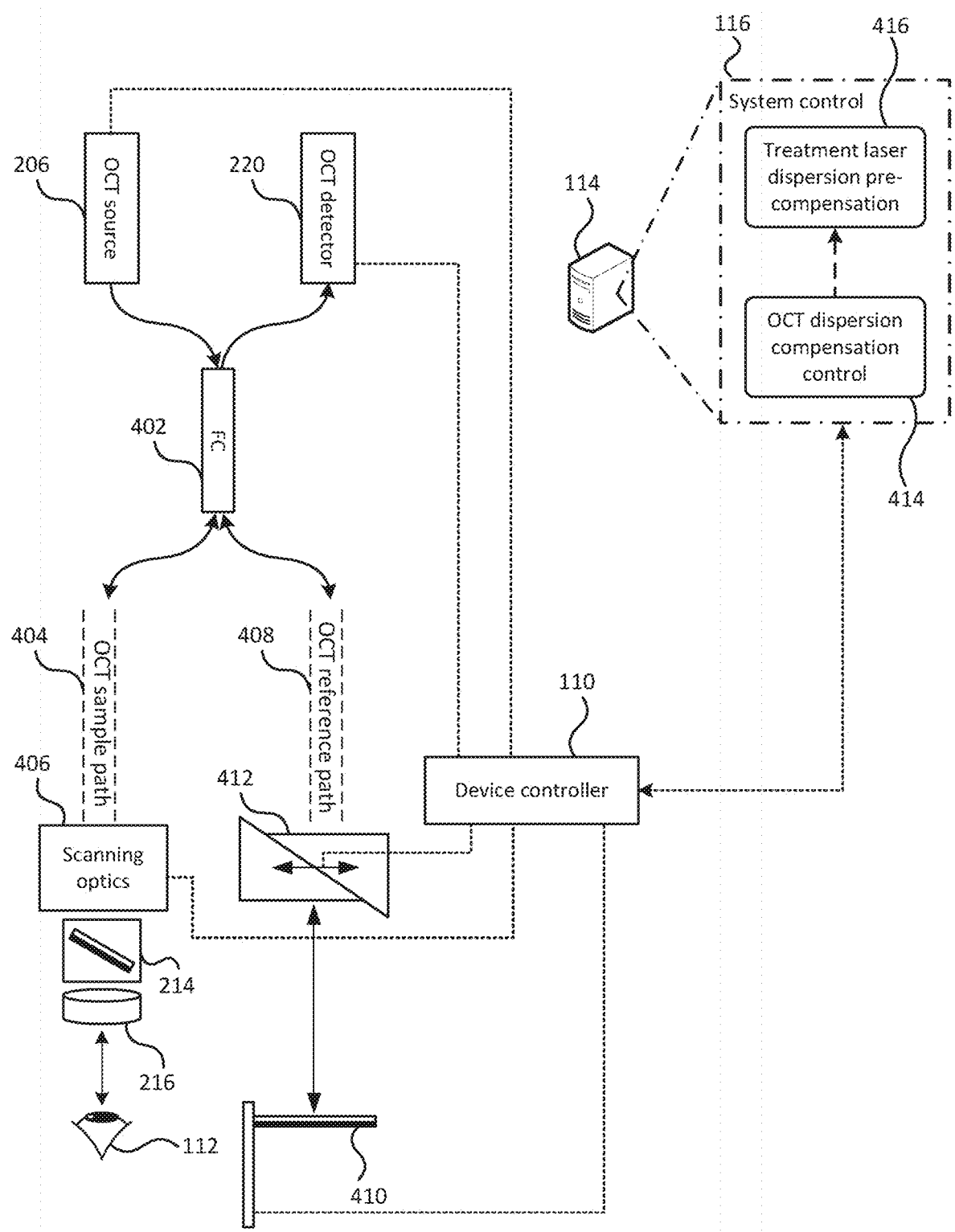
FIG. 4 depicts components of an OCT imaging portion of the imaging and laser treatment system.

FIG. 4 depicts components of an OCT imaging portion of the imaging and laser treatment system. OCT imaging uses an OCT source 206 that may be, for example, a super luminescent diode. The source beam is split by a fiber coupler 402, or other optical components, that is capable of splitting and combining light to and from different ports. The OCT source beam is split by the fiber coupler 402 into a sample 404 that includes scanning optics 406, which can scan the optical beam in both an X and Y direction. The scanning optics 406 may comprise galvos and/or resonators similar to the XY scanning optics 304 of FIG. 3 or other scanning devices. The scanning optics 406 may be controlled by the device controller 11 in a similar manner as described above with regard to the driving circuitry 312 of FIG. 3. The OCT sample path delivers the OCT source beam to an eye or target through the beam splitter/combiner 214 that combines and directs light output from the OCT path and the SLO path to the eye 112 through one or more telescope lenses 216. As described above, the telescope lenses 216 may be moved toward or away from the eye 112, defined as the Z-axis, in order to change a focus point of the OCT source beam on the eye. As described above, a contact lens may be placed on the eye in order to deliver the OCT source beam to the eye. The reflected light returns through the OCT sample path back to the fiber coupler 402 where it is combined with light returning from an OCT reference path and the combined light, or a portion of the combined light, provided to the OCT detector 220. Both the OCT source 206 and detector 220 may be controlled by the device controller 110, which can provide an interface to the computing device 114 to allow the computing device 114 to control operation of the imaging and laser delivery system as well as to receive the captured image data from the OCT detector.

The reference path 408 provides a path for the OCT light beam, or portion thereof that was split by the fiber coupler, that has the same path length as the OCT light beam travelling in the sample path, so that the interference of the combined light from the sample path and reference path provide information which can be used to provide an image of the portion of the eye targeted by the sample path. In order to compensate for changing path lengths of the sample path, which may result from, for example, different targeting/focusing locations within the eye, as well as changes in position of the eye, the reference path may include a mirror 410 that is moveable in the Z-axis in order to lengthen or shorten the path length of the reference path. The moveable mirror 410 reflects the light back through the reference path to be combined with the light from the sample path in the fiber coupler 402. The device controller 110 may synchronize the moveable mirror with the moveable telescope lenses so that movement of the telescope lenses results in corresponding movement of the mirror 410 to maintain the path lengths of the sample path and reference path.

In addition to the moveable mirror, which accounts for changing path lengths of the sample path, the reference path may have dispersion compensation components, depicted as a pair of wedges 412 that can be adjusted to provide a thicker or thinner material for the reference beam to pass through. The dispersion compensation components 412 can be used to account for the optical properties of the eye itself, which may be particularly useful in OCT imaging which may be used to image the back, or retina, of the eye. The dispersion compensation components 412 may be controlled by the device controller 110 in coordination with the computing device 114. In particular, the computing device 114 may include OCT dispersion compensation control functionality 414 that adjusts the dispersion compensation components, for example by moving the wedges in or out to provide a thicker or thinner optical component, in order to provide a focused image captured by the OCT detector. That is, when the dispersion compensation component is properly adjusted to account for the optical properties of the eye being imaged, the image captured by the OCT detector will be in sharp focus. The OCT dispersion compensation control functionality may be based on autofocus techniques which adjust the focusing optics based on a sharpness of the captured image. The dispersion compensation components may be adjusted until a sharp image is produced.

The amount of dispersion compensation provided by the dispersion compensation components 412 may also be used for other purposes in addition to compensating the OCT reference beam. Since the particular compensation provided by the dispersion compensation components, for example the 'thickness' of the component 412, provides an indication of the optical properties of the eye, the particular compensation may be used for other compensation, including for example, post-compensation of SLO images, which may comprise image processing techniques, as well as controlling optical compensation components in order to provide pre-compensation of the treatment laser pulse. The temporal pulse compression and frequency pre-compensation may be performed by, for example, treatment laser dispersion pre-compensation functionality 416, which may adjust pulse pre-compensation components in the treatment optical pathway based on the compensation required to provide a sharp in-focus OCT image as determined by the OCT dispersion compensation control functionality 414.

Figure 5:
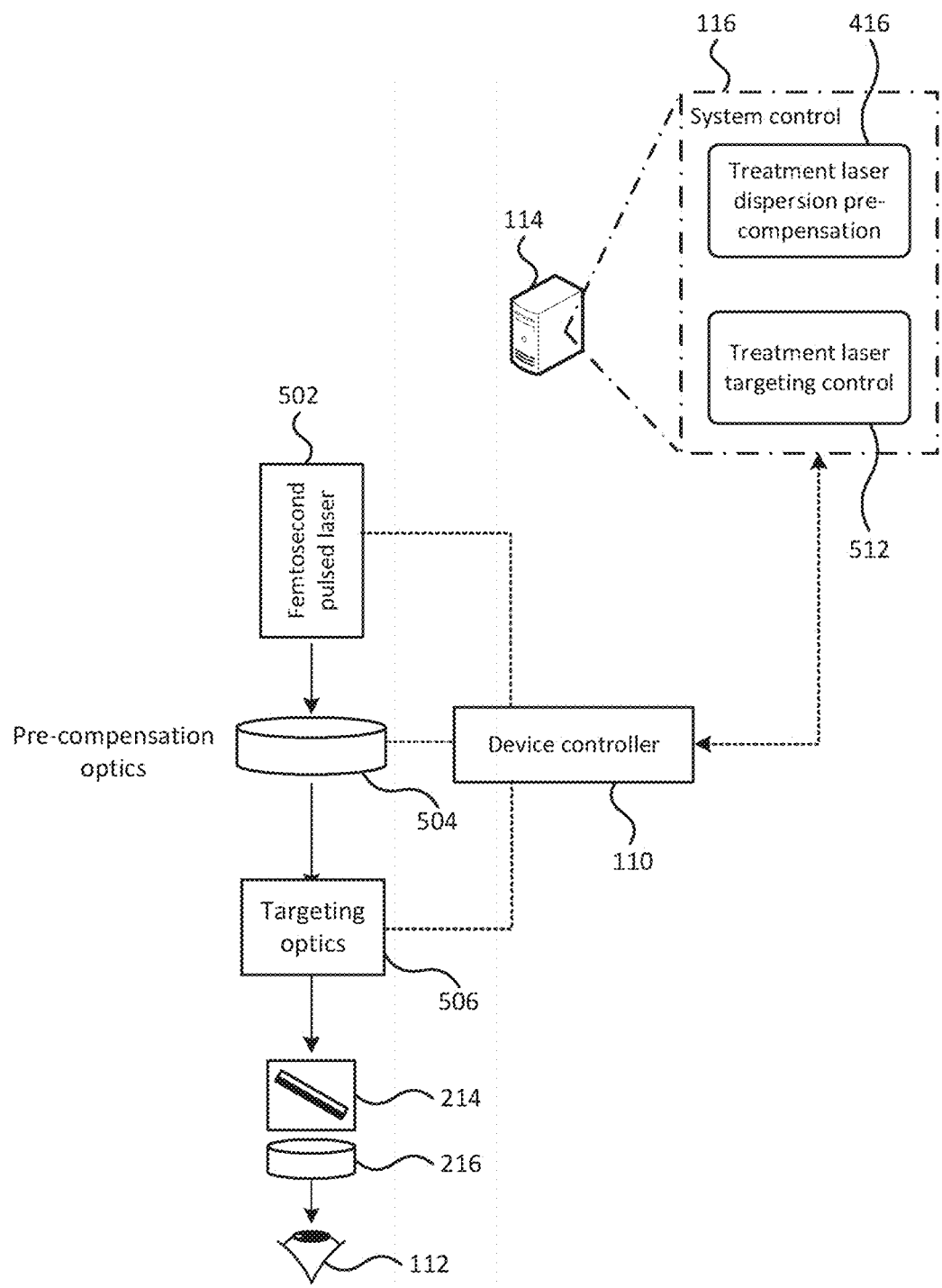
FIG. 5 depicts components of a laser delivery portion of the imaging and laser treatment system.

FIG. 5 depicts components of a treatment laser delivery portion of the imaging and laser treatment system. The treatment laser is depicted in FIG. 5 as being a femtosecond, picosecond, or a nanosecond pulsed laser 502, however other laser sources may be used depending upon the particular application. For example, the treatment laser may be a fiber or free-space femtosecond/picosecond/nanosecond laser gas laser, fiber laser, dye laser, a solid-state laser (pulsed or continuous wavelength), a pulsed or continuous wavelength diode laser, an optical parametric oscillator, an optical amplifier optical, and optical parametric amplifier, or a coherent light generated form nonlinear optical processes (e.g. sum, difference, and second harmonic light generation) etc. The treatment laser may pass through pre-compensation optics 504 and targeting optics 506. The targeting optics allow the treatment laser beam to be targeted at specific locations of the eye requiring treatment by the treatment laser. The targeting optics 506 may be similar to the scanning optics described above for the SLO and OCT optical paths and may comprise for example galvos and/or resonators or other scanning devices, which may be controlled by targeting control functionality 512 on the computing device 114. The treatment beam from the targeting optics passes through the beam splitter/combiner 214 and through one or more telescope lenses 216 that direct the treatment laser beam to the eye 112.

As described above with reference to FIG. 4, the dispersion compensation components 412 may provide an indication of the dispersion that occurs in the eye. Accordingly, the treatment laser dispersion pre-compensation functionality 416 can control, through the device controller 110, the pre-compensation optics 504 in order to pre-compensate the treatment laser beam.

The above has described a system comprising optical components, electronic components and software components, which together provide a system capable of imaging an eye, or other target, using a confocal optical detection system and an optical coherence tomography system and targeting a location within the eye for treatment by a therapeutic laser system. In addition to imaging the eye, the imaging systems may also be used to provide real-time navigation, and eye-tracking allowing for the treatment laser beam/pulse to be accurately targeted.

Figure 6:
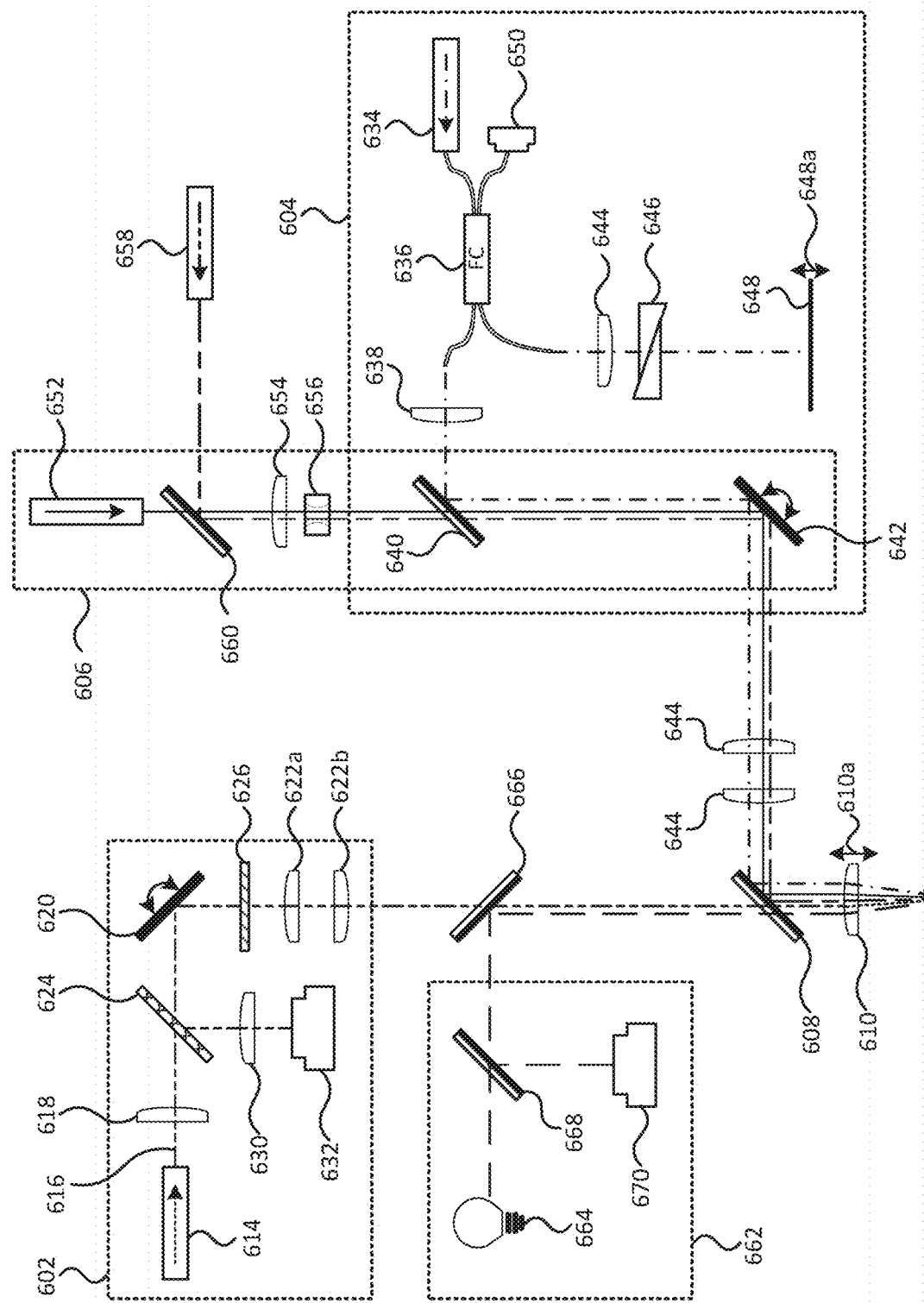
FIG. 6 depict optical components of a further ocular imaging and laser treatment system.

FIG. 6 depicts optical components of a further ocular imaging and laser treatment system. The above system has described the three optical systems, namely the SLO imaging system, OCT imaging system and treatment laser system as using separate scanning/targeting optics. It is possible to combine the targeting optics of the treatment laser with the scanning optics of the SLO or OCT imaging system. Further, it is possible to combine the scanning optics of the SLO and OCT imaging system together, however this may result in a slower frame rate for the SLO imaging system. The slower frame rate may not be sufficient to provide real-time imaging sufficient for eye tracking during treatment laser treatment. Accordingly, the system 600 described below provides separate scanning optics for the SLO imaging components while combing the scanning/targeting optics of the OCT imaging and treatment laser delivery together.

The system 600 comprises SLO imaging components 602, OCT imaging components 604 and treatment laser components 606. The light for each system 602, 604, 606 is combined/split at beam splitting device 608. The combined beam is focused onto the eye by one or more telescope lenses 6110, which may be moveable as depicted by arrow 610a in order to adjust the focus point of the light in or on the eye 612 or target. As depicted, each of the systems may have a different wavelength. As an example the SLO wavelength may be approximately 658 nm, the OCT wavelength may be approximately 800 nm-1200 nm and the wavelength of the treatment laser may be approximately 200 nm-3000 nmnm. Although specific wavelengths have been provided, it is possible to use different wavelengths for each of the SLO, OCT and treatment systems. Additionally, the SLO source could include red, green and blue sources and corresponding detectors or other types of SLO imaging sources.

Regardless of the specific wavelengths, the SLO imaging system 602 comprises a light source 614. The light source may be external to the imaging and delivery device and coupled to the device for example by an optical fiber or free space optics. Regardless of how the light source 614 is provided, it provides a light beam depicted by line 616. The beam passes through focusing optics, as well as scanning optics 620. The focusing optics may include lenses 618 positioned before the scanning optics 620 as well as lenses 622a, 622b located after the scanning optics 620. Although only a single mirror is depicted as the scanning optics 620, it will be appreciated that a pair of mirrors or scanners may be used to provide scanning of the optical beam in both an X and Y direction. The optical beam from the source may also pass through a another beam spiting device, which is depicted in FIG. 6 as a polarizing beam splitter 624 that is capable of splitting light according to its polarization. Although depicted as being located between the scanning optics 620 and the source 614, it is possible to be located in different locations of the optical pathway. The light from the source 614 is directed towards the eye 612 through a polarizing element 626, such as a quarter or half-wave plate, that changes the polarization of the light passing through it. The light is directed to the eye and the reflected off the eye returns through the same path and again passes through the polarizing element 626 which again changes the polarization of the returning light so that the returning light has a different polarization from the source light and so can be separated from each other by the polarizing beam splitter 624. Other optical devices than a polarizing beam splitter and polarizing element can be used to separate the returning reflected light from the source light, such as for example an optical circulator. The reflected light returning from the eye passes through one or more focusing optics 630a, 630b, which focuses the beam onto a detector 632 which may be an avalanche photo detector or similar device. It will be appreciated that the scanning optics may sweep the beam across the eye in the X and Y direction and the resulting output of the detector at each coordinate can be used to construct a raster image of the eye.

The OCT imaging system similarly comprises a light source 634, which may be for example one or more super luminescent diodes. The light from the source passes through a fiber coupler (FC) 636. The fiber coupler can split light and combine light received on different ports. For example incident light from ports 1 and 2 may be combined and the combined light split to be output from ports 3 and 4. Similarly incident light from ports 3 and 4 is combined and output at ports 1 and 2. The FC 636 splits the light from OCT source 634 into a sample path and a reference path. Light from the FC 636 in the sample path may pass through one or more focusing lenses 638. A beam splitter/combiner 640 is used to combine/split the light from the OCT source with/from the treatment light source. The combined light pass through scanning/targeting optics 642 that can scan the light beam in both the X and Y directions.

The light from the FC 636 is also directed to a reference path that may pass through one or more focusing optics 644, compensation optics 646 before reflecting off of a mirror 648. The mirror 648 may be moveable in a direction depicted by arrow 648a in order to adjust the length of the reference path to match the length of the sample path. Light returning from both the sample path and reference path are combined together at the fiber coupler 636 and the combined light passed to a sensor 650, which may be for example a CCD sensor. Additionally or alternatively, the detector may be provided by an APD may be used with swept source OCT. Although not depicted, one or more optical elements, including filters, lenses, gratings, etc. may be located in front of the sensor 650.

The treatment laser delivery system 606 comprises the treatment light source 652, one or more focusing optics 654 as well as pre-compensation optics 656 which may be controlled by the device controller (not depicted). As depicted, the combined light from the treatment laser and the OCT source are combined together and pass through the same scanning/targeting optics 642. In addition to the treatment light source, the system may include a pilot laser 658, that may be combined with the treatment laser 652 by a beam splitter 660. The pilot laser 658 may pass through the optical path way of the treatment laser and may be used to ensure the treatment laser is properly aligned and targeted. The pilot laser, and in particular the location of the focusing of the pilot laser within the eye may be detected by one or more of the imaging systems.

The imaging systems have been described above as comprising a SLO imaging system 602 and an OCT imaging system 604. In addition to the SLO and OCT imaging systems, additional imaging systems may be incorporated into the system. As depicted, a fundus imaging system 662 may be included, as well as for example a fixation target system (not depicted) that can provide an LED or other feature for focusing on. The fundus imaging system may include a suitable light source 664, which can be combined with other light sources by a beam splitter 666. Although depicted as being combined with the SLO imaging light, the fundus imaging light may be combined with outer light sources at other locations. The returning light is split by a beam splitter or similar device and directed to a camera sensor 670 that captures the fundus image. The fundus image may be illuminated by a broad spectrum light source and the sensor may include red, green, and blue sensors for capturing a colour image. Alternatively, the fundus image may be illuminated by specific frequencies or frequency ranges.

The combined light from the OCT imaging and therapeutic systems, as well as the pilot laser and fundus imaging light, is combined with the light from the SLO imaging system by the beam splitter 608. The combined light from all of the systems passes through the telescope optics 610 which may be moved in the Z direction, towards or way from the eye, to change the depth of focus. Light from the treatment laser is absorb by the tissue eye which causes some change in the eye, such as photocoagulation, incisions in the tissue, ablation, etc. Light from the SLO and OCT imaging systems, as well as the fundus imaging system and pilot laser, are reflected back from the eye and is separated and directed to the respective optical path. The reflected light passes through each optical path to the respective sensor, i.e. the SLO sensor 632 or the OCT sensor 650.

Although numerous optical elements have been depicted above, additional optical elements may be included in the system. For example, one or more filters may be provided at different positions in the optical paths in order to block certain wavelengths. Additionally, apertures may be provided to further block unfocused light. Additionally, one or more sensors may be located along the optical paths in order to determine, and possibly adjust alignment of light from one or more of the sources. Additionally, while a single treatment light source is described, it is possible to have multiple different treatment light sources, or to have interchangeable light sources allowing one treatment light source to be replaced with a different treatment source. Additionally, although the treatment source has been described as being used for carrying out a particular treatment, it is possible for the treatment source to be used in imaging the eye along with carrying out the particular treatment.

The above has described a system capable of simultaneously imaging an eye using both a SLO imaging system and an OCT imaging system while also delivering a treatment laser to a targeted location in the eye. The system may be controlled by software in order to provide various imaging, treatment planning, and treatment performance functionality.

Figure 7:
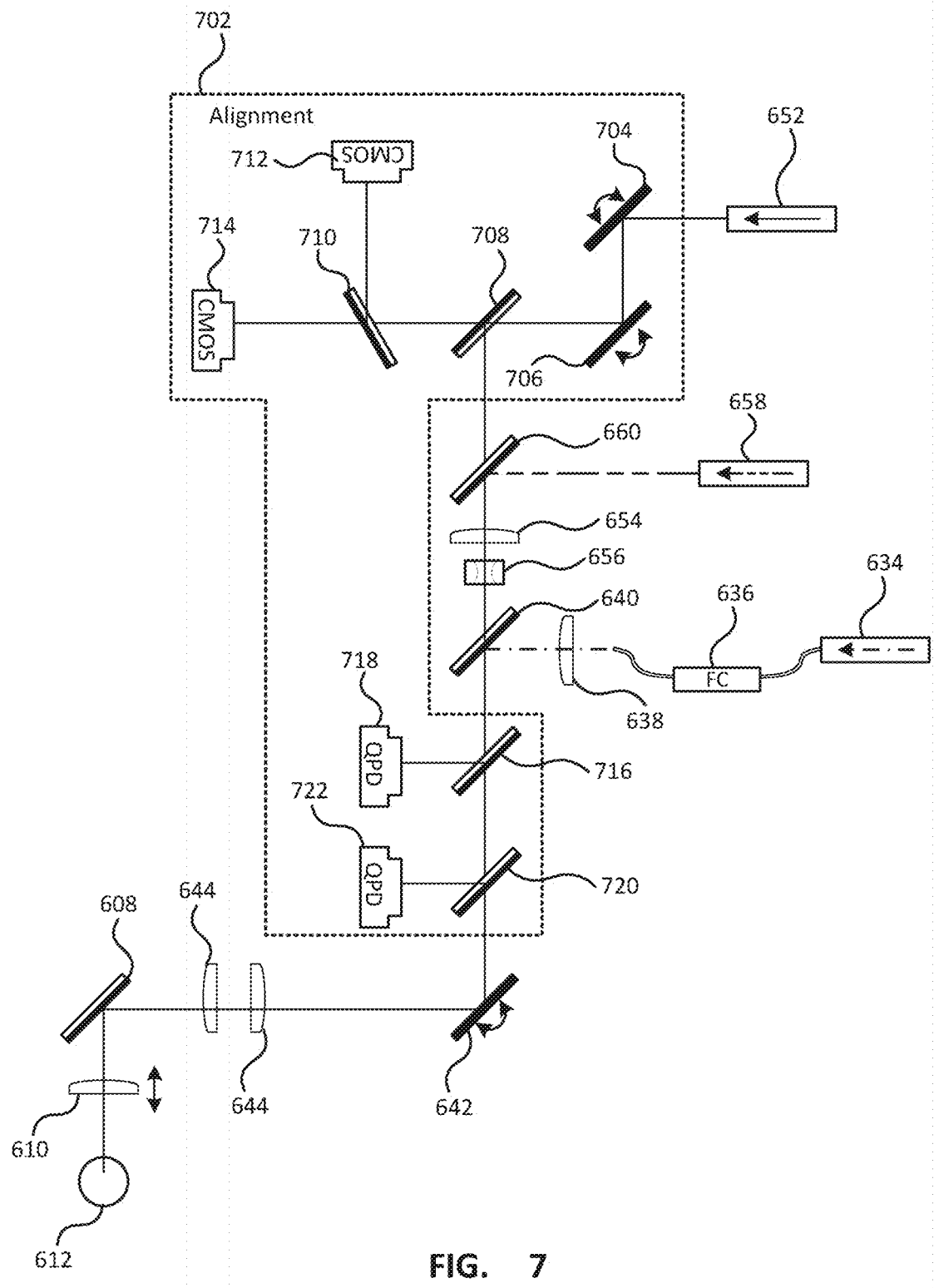
FIG. 7 depict optical components of an alignment system.

FIG. 7 depict optical components of an alignment system. The alignment system 700 may be incorporated into any of the embodiments described above, however is described below with particular reference to the components of the OCT system 604 described in reference to FIG. 6. It is noted that the components of the OCT reference path and sensor have been omitted from FIG. 7 for simplicity. The alignment system 702 allows the therapeutic laser to be aligned, or at least substantially aligned, with the OCT laser. When the therapeutic laser is fully aligned with the OCT laser the two laser beams or pulses will be coincident with each other along their entire path. The alignment system may also be used to align the therapeutic laser with an input fiber or port. For example, if the therapeutic laser is a femtosecond laser, the source may be coupled to the imaging and treatment system using an optical fiber such as a hollow core fiber or kogami fiber, which may have a small numerical aperture which may require active alignment in order to inject the laser pulse into the fiber. Additionally, aligning the therapeutic laser with the OCT laser helps to align the target locations determined using in part the OCT image with the actual treatment location. The alignment system 702 may comprise a coarse alignment system that can align the laser source for proper injection into the coupling component, which may be an optical fiber or free-space optics such as an articulated arm and mirror assembly. In addition to the coarse alignment, fine alignment may be provided using sensors along the OCT path.

The coarse alignment components may be located at the output of the therapeutic source 652. The therapeutic beam passes through two adjustable mirrors or other positioning optics 704, 706. Although not depicted in FIG. 7, the positioning optics 704, 706 are controllable by a controller in order to be able to control the alignment of the therapeutic beam. The positioning optics 704, 706 may be arranged in a Z-fold arrangement, a figure-4 arrangement or any other type of arrangement suitable for aligning the therapeutic beam. After passing through the positioning optics 704, 706 the therapeutic beam passes through a beam splitter 708 that directs a portion of the beam to coarse alignment sensors and the other portion to the optical coupler of the OCT path. The beam splitter 708 may be an asymmetric splitter so that only a small portion of the therapeutic light is spit to the alignment components. For example the beam splitter 708 may be 99:1 splitter. The light split for alignment is further split by a second beam splitter 710 for directing the light into two separate paths that terminate at sensors that can determine the incident location of the light in two orthogonal axis, such as the X and Y axis. The sensors are depicted as being CMOS sensors 712, 714 which provide a relatively large sensor area in order to be able to detect the incident location even if the beam is relatively poorly aligned. Although not depicted in FIG. 7, the coarse alignment sensors 712, 714 are coupled to a controller that controls the positioning optics 704, 706 in order to move the incident location of the laser to be centered in both alignment sensors 712, 714. The path lengths to the two sensors should be different, with a longer path length providing greater alignment accuracy.

In addition to the coarse alignment, a fine alignment sensors may be provided for providing a more precise measurement of misalignment. A beam splitter 716 may be located in the OCT path an may split the beam to direct a portion of the beam to a first quadrature photodiode (QPD) 718, which can be used as a precise alignment sensor. A second beam splitter 720 may be located in the OCT path as depicted, or alternatively in the alignment path from the splitter 716 similar to the arrangement for the course alignment. Regardless, a second path to a second QPD 722 is provided. As with the coarse alignment the path lengths to each QPD 718, 722 should differ to ensure the path of the beam is aligned along the path. That is, if the path lengths were the same, the sensors would only confirm that the path was aligned at the particular location, but the beams could be diverging or converging from the point. The controller (not depicted) controls the positioning optics 704, 706 in order to arrange the incident location on both QPD sensors to be in the middle, or as close to the middle as necessary to achieve the desired precision in the alignment.

It is noted that FIG. 7 only depicts the optical components and omits the control components. As will be appreciated, the sensors 712, 714, 718, 722 are coupled to a controller that determines the adjustments that need to be made in order to align the beams according to the sensor data. The controller may then control the operation of the moveable mirrors or positioning optics 706, 708 in order to align the therapeutic laser with the OCT laser. The controller controls the positioning optics 706, 708 so that the incident location of the therapeutic laser is at the center of each of the sensors 712, 714, 718, 722, or at least attempts to position the incident location as close to the center as possible. The alignment system may constantly correct the alignment of the therapeutic laser. Alternatively, the alignment may be performed at specific times or intervals, such as before treatment, upon startup, daily, etc.

Control of the alignment process may be accomplished without any knowledge of the geometry of the optical pathway. The alignment process may use, for example, a positive reinforcement learning algorithm in order to control the positioning optics in order to converge the laser beam onto a specific point on each sensor, such as the center. The alignment algorithm may make adjustments to the positioning optics, measure the resulting laser beam position on the sensors and use the feedback to further adjust the positioning optics according to the alignment algorithm.

In addition to aligning the laser according to the sensor 712, 714, 716, 720 information, the system may also be aligned using real-world feedback. For example, a model of the eye, such as a plastic eye or other suitable material, may be positioned within the system and the imaging system used to target a specific location. The therapeutic laser may be fired at the targeted location and the result of the therapeutic laser on the model eye detected and any discrepancy between the target location and the actual incident location can be corrected for, for example using the alignment mirrors or positioning optics 706, 708. The real-world alignment may be performed periodically, such as before treatment, upon startup, daily, etc.

Although the above has described the use of coarse and fine alignment sensors for aligning the therapeutic laser to be at the center of the alignment sensors, the alignment sensors, and in particular the fine alignment sensors may be used to align the pilot laser. The fine alignment sensors may be used to co-align the pilot laser and the therapeutic laser in a similar manner as aligning the therapeutic laser described above.

The therapeutic lasers and the pilot laser may be aligned as described above. Further, the pilot laser and/or the therapeutic laser may also be aligned with the SLO imaging system and/or the OCT imaging system. For example, the pilot laser, or the therapeutic laser, may be scanned over the patient's eye, or a model of the eye, and then detected by the detector of the SLO imaging system and or the detector of the OCT imaging system. The pilot laser, or the therapeutic laser, may be scanned through known positions and the known positions of captured by the SLO imaging system and/or the OCT imaging system. The captured pilot laser's position, or the therapeutic laser's position, may then be used to align the pilot laser, and/or therapeutic laser, and the SLO imaging system or OCT imaging system. The alignment may be done using software-based image registration.

FIG. 7 depicts the pilot laser 758 being combined with the treatment laser 652 after the coarse alignment components. It is possible for the pilot laser to be combined with the treatment laser prior to the coarse alignment. The pilot laser and the treatment laser may be combined and input into the coarse alignment from a single fiber.

Figure 8:
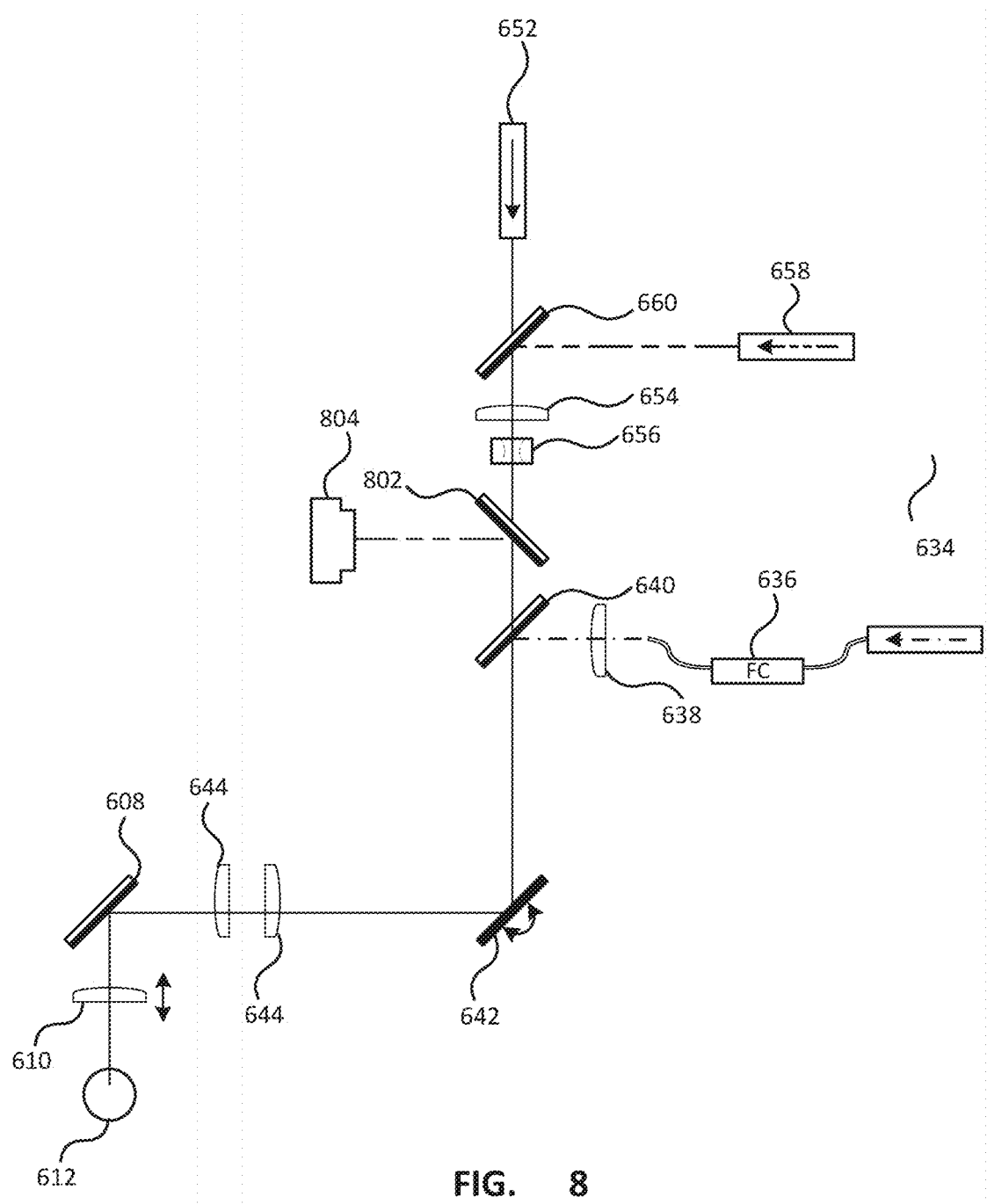
FIG. 8 depicts a further arrangement for aligning the components of a laser imaging and delivery system.

FIG. 8 depicts a further arrangement for aligning the components of a laser imaging and delivery system. The alignment system 800 may use a pilot or therapeutic laser for aligning with the SLO and/or OCT imaging components. The pilot laser alignment described above detected the pilot laser, or treatment laser, using either, or both, the SLO detector or OCT detector. However, it may not be possible to detect the pilot or therapeutic laser using the SLO or OCT detectors. In such a case, a beam splitter 802 may be provided to split the returning pilot laser or treatment laser and directs a portion to a detector 804 such as an avalanche photodetector (APD). The pilot alignment system 800 may include additional optical components for focusing the pilot/treatment laser at the APD 804. The pilot laser or treatment laser may be scanned across the eye using the scanning/targeting optics 642 and the signal captured by the APD 804 at each scanning position used to generate an image of the eye. The generated image from the APD 804 and the pilot/treatment laser may then be registered to other images of the eye such as a SLO image. The registration between the pilot image and the SLO image may be performed using image registration techniques to correlate between the position of the pilot/treatment laser and the SLO image. A similar process may be used to register with OCT images.

Figure 9:
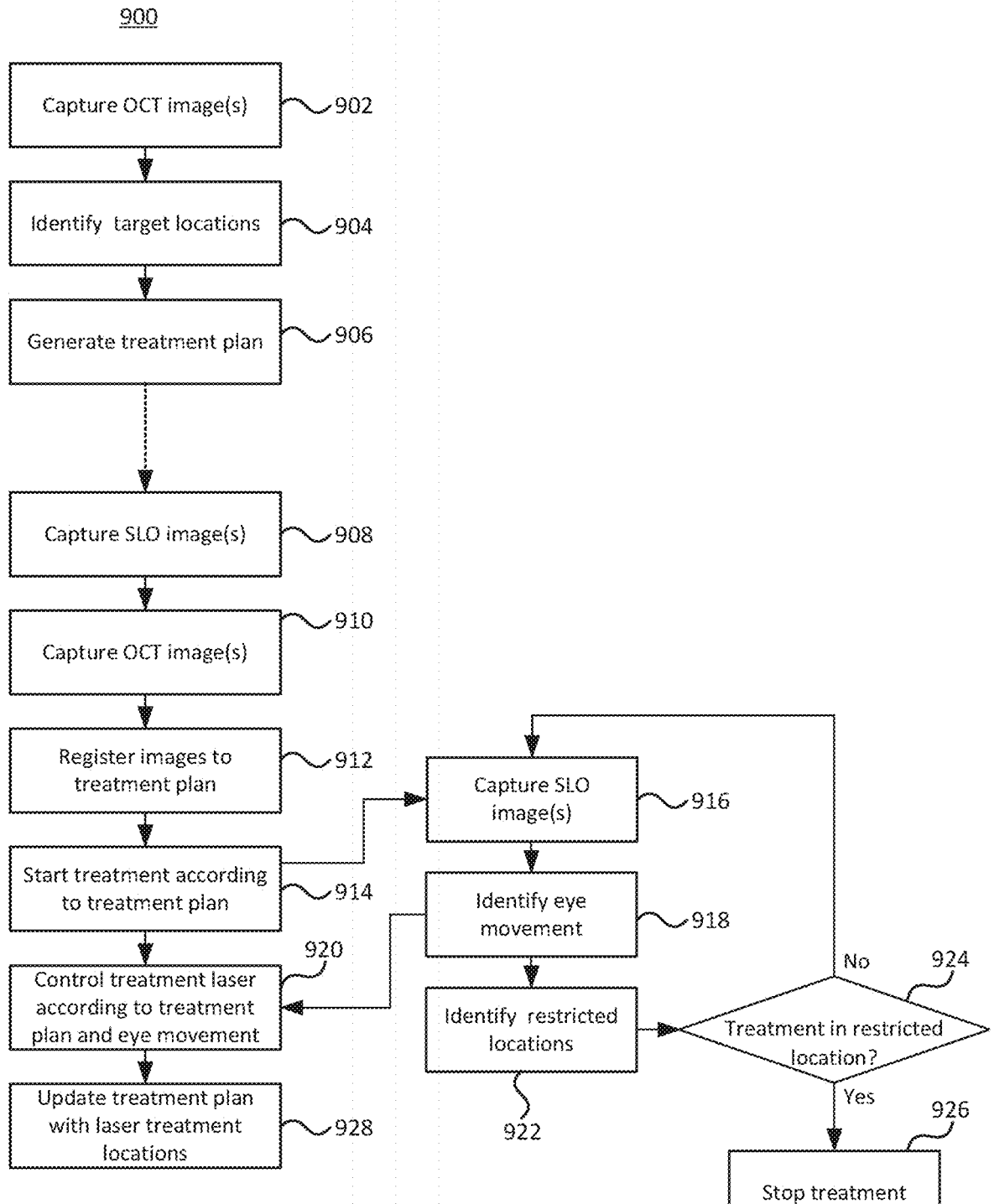
FIG. 9 depicts a method of planning and performing a treatment for an ocular condition using an ocular imaging and laser treatment system.

FIG. 9 depicts a method of planning and performing a treatment for an ocular condition using an ocular imaging and laser treatment system. The method 900 begins with capturing OCT images (902) along with other possible images, including for example SLO images, fundus images, flourescin angiography, or other images of the eye. The images may be captured by the imaging and delivery systems described above, or they may be captured by separate imaging systems and possibly taken at different times. The images are registered to each other using image processing techniques to identify corresponding features in the images and align or transform the images to be registered together. One or more target locations can be identified (904) in the registered images. The target locations are locations within the eye that are to be targeted for treatment by the treatment laser. The target locations can be identified manually by an ophthalmologist or other professional. The target locations may be identified in the registered images using drawing tools or other techniques that allow the treatment locations to be specified. Additionally, or alternatively the target locations may be identified within the images using automated processes which if required may be presented to a treatment provider for approval or adjustment. In addition to the identified target locations, the laser parameters, such as power, pulse duration, pulse frequency, a treatment time, repetition, etc. are also specified for each target location. The target locations and associated laser parameters are used to generate a treatment plan (906) that specifies how the laser will be operated for the treatment of an eye condition. The treatment plan, which may specify the treatment locations using Cartesian coordinates, or other 3 dimensional coordinate system, may be stored in association with one or more registered images, allowing the treatment plan, and so treatment locations, to be accurately re-aligned to the eye by registering the eye position to the images of the treatment plan.

As described above, the treatment plan may be generated while the individual being treated is located in the imaging and laser delivery system, or may be generated from separately captured images. Regardless, at some point after generating the treatment plan, the individual will be located in the imaging and laser delivery system and the system will begin to capture SLO images (908), fundus image, and OCT images (910) the newly captured images are registered against the previous images of the treatment plan (912). It is not necessary to register all of the images together and it is possible for proper alignment to be provided by registering the SLO image to the treatment plan. If the treatment plan images were previously captured by separate imaging systems, this may use imaging processing techniques to identify corresponding features within the images in order to register them to each other. Alternatively, if the treatment plan was generated while the individual was located in the imaging and laser delivery system, the registration may be done, for example by adjusting the registration based on eye movement. After registering the images to the treatment plan, the alignment may be verified prior to treatment using a pilot laser to ensure that the pilot laser that passes through the treatment laser optical path is properly aligned and so the treatment laser is aligned as well. Regardless, once the newly captured images and treatment plan images are registered, the treatment according to the treatment plan can begin (914). Although not depicted in FIG. 9, the imaging and treatment system may be periodically calibrated to register coordinate systems across different imaging components. The calibration may be performed each time the system is used, or may be performed less often such as each day, week, etc. The treatment plan may be presented or displayed over the real time images and the treatment plan confirmed prior to beginning treatment. The user may be provided with an interface that allows treatment parameters to be adjusted by the doctor during the treatment. During treatment, the system may continuously capture SLO and fundus images (916), which are captured in real-time at a relatively high frequency, to identify eye movement (918). The identified eye movement may be used to adjust the target location of the treatment laser in order to target the correct location within the eye according to the treatment plan while accounting for the eye movement (920). If the tracking of the eye movement provides unreliable results, for example the movement is unrealistically large, or a confidence level of the eye tracking is low, the treatment with the laser may be stopped until the tracking results are reliable. Although not depicted in FIG. 9, it is possible for the system to also capture OCT images during the treatment phase in order to allow the treatment to be monitored in real time. The monitoring may be done manually by a treatment provider, or automatically or semi-automatically by one or more algorithms. The monitoring may be used to adjust treatment parameters during the treatment, stop the treatment prematurely, or continue the treatment at the particular location further than specified by the treatment plan. Controlling the treatment laser may include verifying that the system is running properly, and that the status of all of the components is acceptable. If the system status is not good, the firing of the laser may be prevented.

In addition to identifying and tracking eye movement, the method may also process the captured SLO images in order to identify restricted locations within the eye (922) that are not safe for treatment with the treatment laser. It is possible to identify restricted locations, such as the optic nerve, and the macula manually during the planning of the treatment. It will be appreciated that different regions may be identified as restricted regions for different treatment types. For example, during treatment for age-related macular degeneration the optic nerve may be identified as a restricted location, whereas, during other treatment such as treatment of the optical nerve, it may not be identified as a restricted location. Additionally or alternatively to identifying the restricted locations during the planning phase, the restricted locations may be identified automatically during the treatment using image processing and machine learning techniques. Identifying restricted treatment locations from the real time captured images may allow for identifying dynamic regions that should be restricted from treatment as opposed to static regions or locations such as the optic nerve. For example, a treatment region that was considered safe for treatment during the planning stage may appear to be unsafe for further laser treatment, and so be identified as a restricted region, as a result of the treatment. For example, the treatment may cause some damage to the tissue which is above an acceptable threshold and as such any further treatment at that location would be unsafe. Once the restricted locations are identified, whether automatically during treatment or manually during the planning phase or possibly automatically during the planning phase, it is determined if the treatment is to occur in the restricted location (924) and if it is (Yes at 924) the treatment is stopped (926). Stopping the treatment may involve simply controlling the treatment source to not deliver the treatment light. Additionally or alternatively one or more backup redundancies may be provided, such as shutters, flip mirrors, etc. may be provided to ensure that the treatment light does not reach the eye. If the treatment is not in an unsafe location (No at 924), the treatment continues and the images may continue to be captured and processed.

Once the treatment plan is completed, the treatment plan can be updated (928) with information about the actual treatment performed as well as images captured after the treatment was completed. Although the treatment plan is described as being completed in a single session, it is possible that the treatment plan be carried out over multiple separate sessions, in which case the post-treatment images may be used to re-align captured images for the next session and verify the locations of previous treatment locations.

Figure 10:
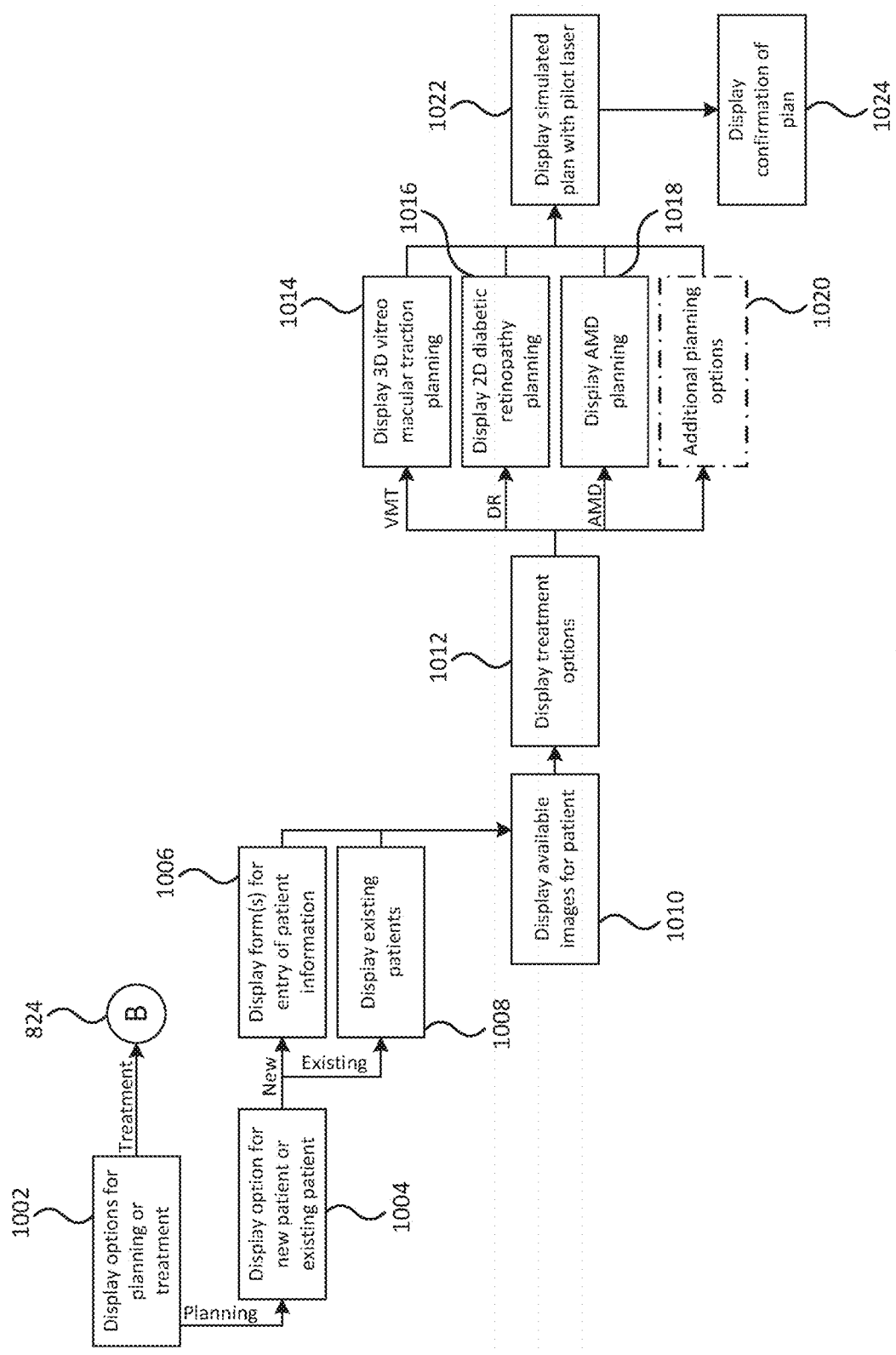
FIG. 10 depicts a graphical user interface flow for planning and performing a treatment for an ocular condition.
Figure 11:
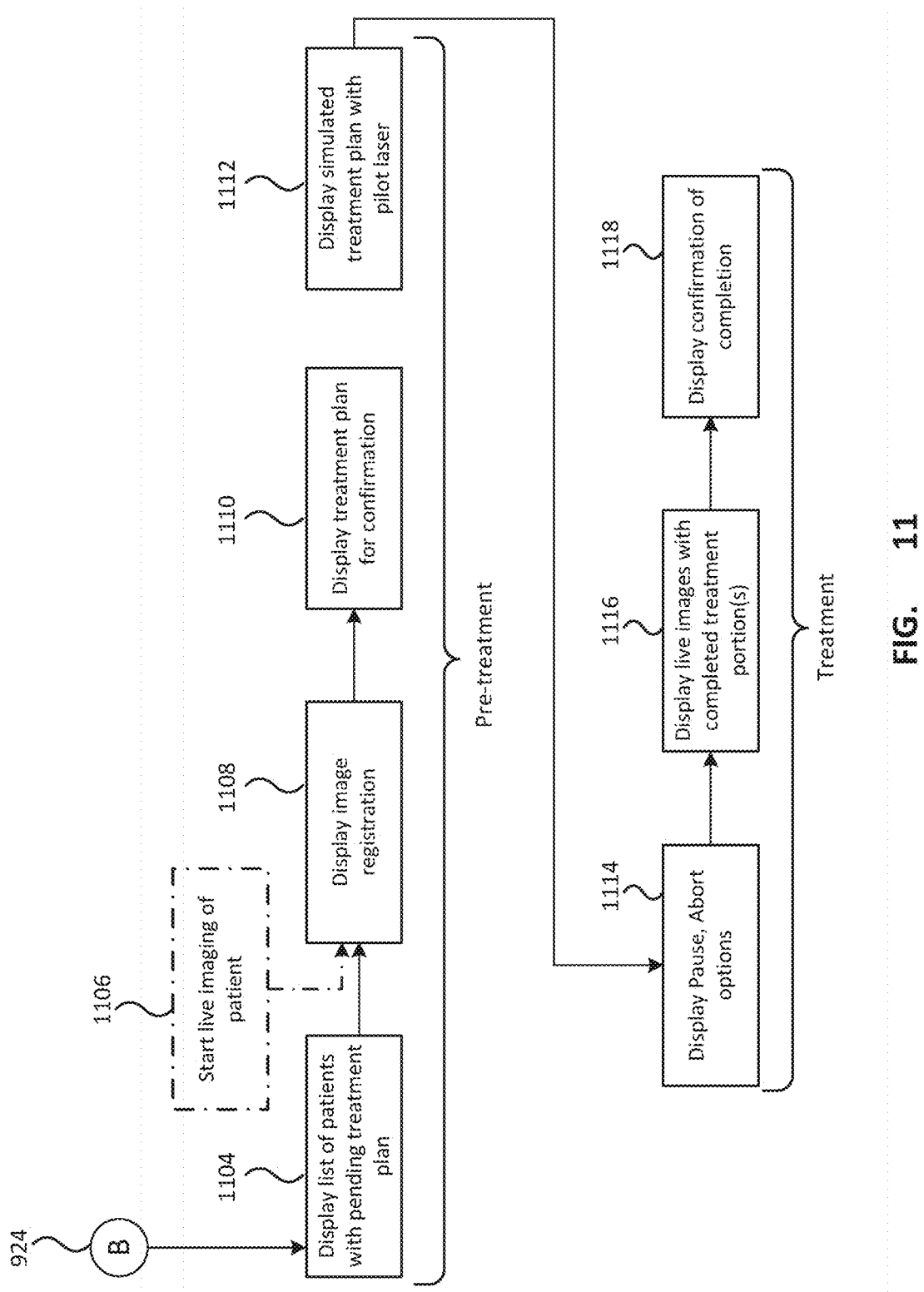
FIG. 11 depicts a further graphical user interface flow for performing a treatment for an ocular condition.

FIG. 10 depicts a graphical user interface flow for planning and performing a treatment for an ocular condition. The system may provide a user interface for allowing a provider, such as an ophthalmologist, to interact with and control the system, including for example to generate a treatment plan for a patient as well to carry out a generated treatment plan. The user interface may be provided in numerous ways and the interface flow depicted in FIGS. 10 and 11 is intended only to be illustrative of one such interface. The user may initially be presented with options to select either planning or treatment functionality (1002). If the user selects the planning option the interface may present the user with an option for selecting an existing patient or adding a new patient (1004). If a new patient is to be added, forms may be displayed for entering patient information (1006), including for example, patient name, medical records, images, insurance information, etc. If an existing patient is to be selected, the existing patients may be displayed or presented in a manner that allows existing patients to be searched and one selected (1008). Regardless of if a new patient is entered or an existing patient selected, the available images for the user may be displayed (1010) and one or more treatment options presented (1012). The system may be provided with various treatment functionality which allows different eye conditions to be treated. Each treatment type may present images or information in a different manner most suited to the particular treatment. The user may be presented with the different treatment options for selection (1012). Additionally or alternatively, the system may have functionality for processing the images and identifying a possible eye condition and then automatically select the corresponding treatment planning options. As depicted depending upon the treatment type selected, different treatment planning may be displayed, for example, for vitreomacular traction planning (1014) which may best specify the treatment plan using a 3D image of the eye, diabetic retinopathy planning (1016) which may best specify the treatment plan using a 2D image of the eye, age-related macular degeneration (AMD) planning (1018), which may display 3D images of the eye, or 2D images with one or more cross-sectional images, or other treatment planning options (1020). Each of the treatment options may present the user with tools for planning a treatment path and/or may automatically determine and present a recommended treatment plan. If the treatment plan is generated while a patient is in an imaging and treatment system as described above, it may be possible to display a simulated treatment plan on the real time images, using the a pilot laser instead of the actual treatment laser (1022). Regardless of how the treatment plan is generated, the user interface may display a simulated treatment confirmation to the user for accepting the treatment plan (1024).

If the user selects the treatment option instead of the planning option at (1002), the interface flow proceeds to the flow depicted in FIG. 11.

FIG. 11 depicts a further graphical user interface flow for performing a treatment for an ocular condition. The treatment interface may begin with displaying a list of patients with pending treatment plans, or if the treatment is for the individual continuing on from the planning phase, the interface may simply display the information for the current user.

Once the individual for the treatment is selected, live imaging using the SLO and possibly the OCT imaging systems starts (1106) and the registration of the newly captured images against the treatment plan images can be displayed (1108) along with an option to confirm the registration and starting of the treatment (1110). In addition to displaying the treatment plan, the treatment plan may be simulated using a pilot laser and displayed (1112) for verification that the treatment locations, simulated using the pilot laser, are targeting correct locations on the real time images.

Once the treatment starts, options may be displayed for pausing and/or aborting the treatment (1114). During treatment the live images, which may include both the SLO and OCT images, can be displayed along with an indication of the completed portions of the treatment plan (1116). Once the treatment plan is completed, or if the treatment is completed a confirmation of the completed treatment may be presented (1118).

It will be clear that the interface flows described with reference to FIGS. 10 and 11 are intended to be illustrative and more options may be presented, with a different flow, different information, etc. depending upon what is desired for the system.

Figure 12:
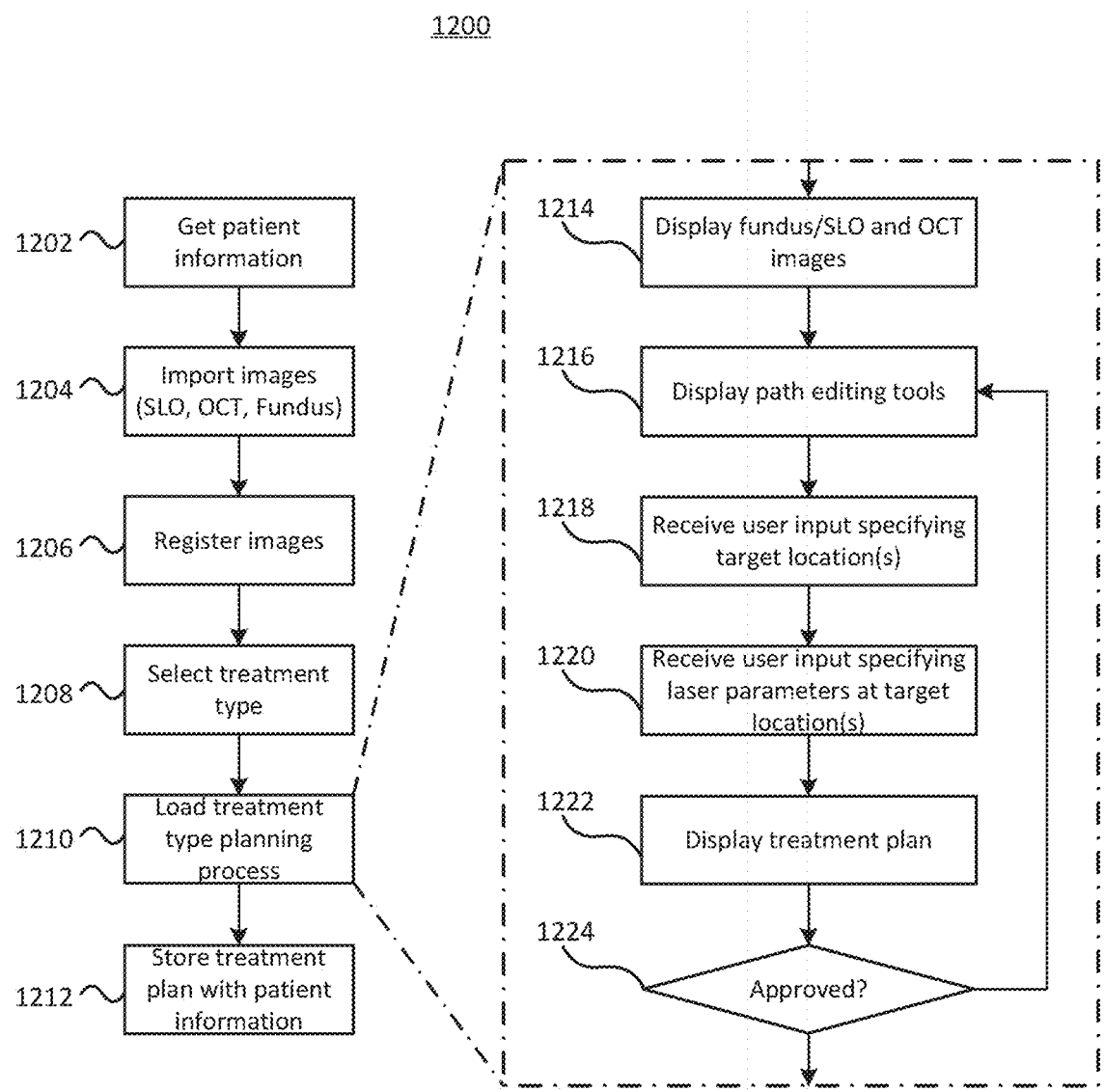
FIG. 12 depicts a method for planning an ocular treatment of an ocular condition.

FIG. 12 depicts a method for planning an ocular treatment of an ocular condition. The method 1200 may be performed by the computing device of an imaging and laser delivery system. The method begins with receiving patient information (1202), which may be input by a user, or retrieved from one or more different databases or information sources. Images of the patient may be imported or captured (1204). The images may vary depending upon the condition being treated and may include for example, SLO images, OCT images, fundus images, etc. The images may be captured separately or may be captured by the imaging and laser delivery system. The images are registered (1206) and the treatment type selected (1208). The particular treatment may be selected based on the treatment functionality available to the system. The treatment type may be selected manually from available treatment types or it may be selected automatically by identifying potential eye conditions present in the registered images and then selecting an appropriate treatment type. The treatment planning process may then be loaded for the particular treatment type (1210) and the treatment plan generated and stored along with the patient information (1212).

Different treatment types may be planned in various ways. Further, it may be possible to automatically generate a treatment plan for different conditions. For example, vitreomacular traction may have automatic planning functionality that may be loaded and processes the registered images in order to identify a location or locations that require laser treatment in order to sever the partially attached vitreous. The automatically generated treatment plan may be presented for approval and/or adjusting.

Additionally or alternatively, the planning may involve manually specifying the treatment plan. Such a scenario is depicted in FIG. 12. The images, such as the fundus/SLO and/or OCT images may be displayed (1214) along with path editing tools (1216) that allow a user to draw or otherwise specify locations within the images. User input is received that specifies the target location(s) using the path editing tools (1218). The specified locations may be associated with laser parameters (1220) that define the particular treatment laser treatment to apply at the particular location. The laser parameters may be individual specified for each location, or the laser parameters may be specified for groups of locations. The generated treatment plan may be displayed to the user (1222), for example as an overlay on the displayed images. If the treatment plan is approved (Yes at 1224) the treatment plan may be stored with the patient information (1212). If the plan is not approved (No at 1224) the editing tools may again be presented to allow the user to continue editing the plan. It will be appreciated that a treatment plan may be modified, for example by adding or removing treatment locations, laser parameters, etc. even after a treatment plan is approved.

In displaying the treatment plan, the system may perform one or more checks to determine if the plan has any possible issues, such as over-applying a laser treatment to a particular area, treatment in a possibly unsafe location, treatment in a location with no identifiable possible conditions, etc. Any possible issues that are automatically detected may be presented to the user for confirmation or correction.

Figure 13:
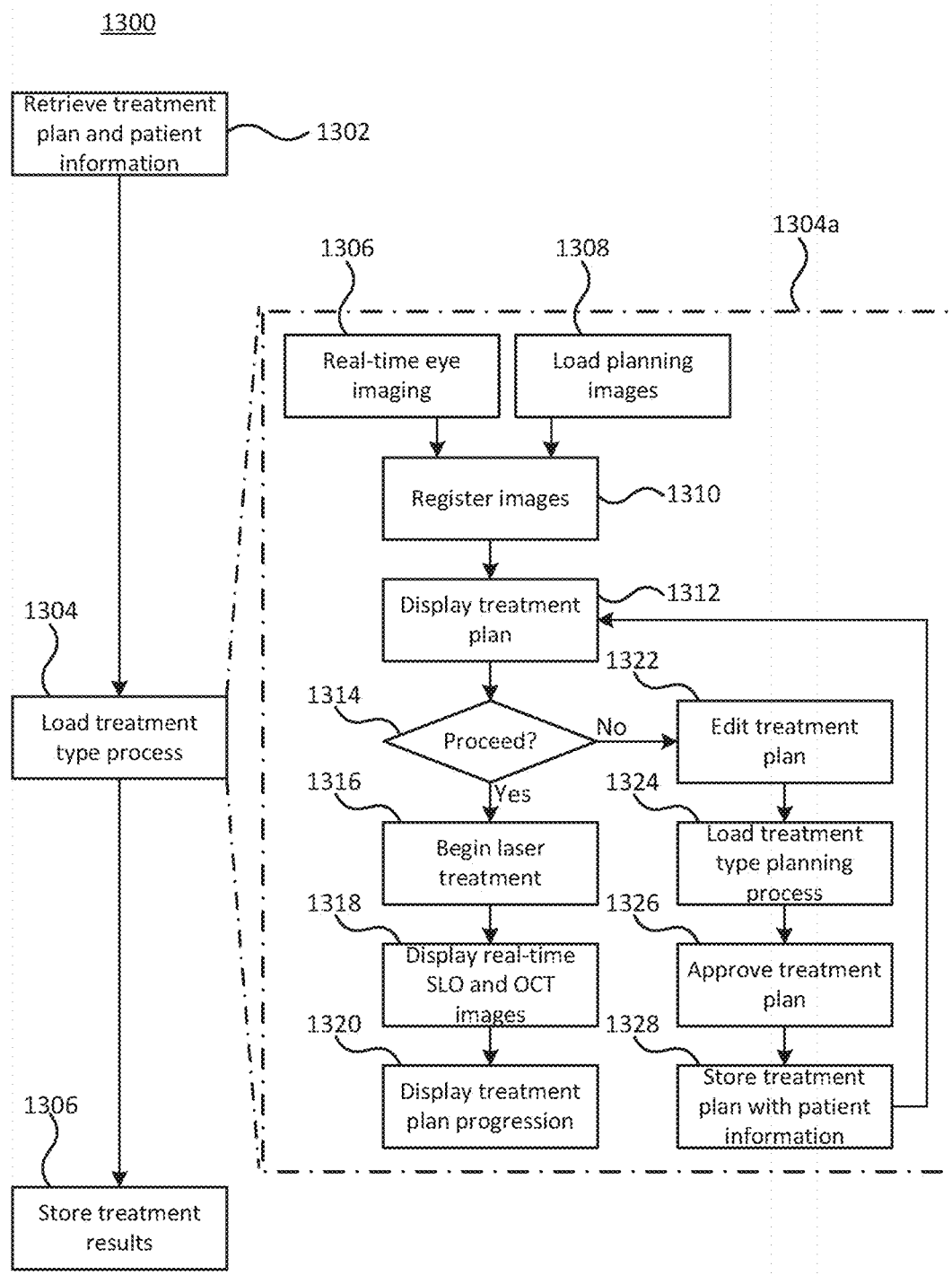
FIG. 13 depicts a method of treating an ocular condition.

FIG. 13 depicts a method of treating an ocular condition. The method 1300 begins with retrieving a stored treatment plan and patient information. The treatment processing functionality for performing the particular treatment of the treatment may be loaded (1304) and the treatment carried out according to the treatment plan. Once the treatment plan is completed, the results of the treatment plan along with one or more images captured during the treatment procedure can be stored (1306). The functionality for performing a treatment may be relatively simple and simply comprise functionality for operating the treatment laser according to the specified laser parameters focused at the particular treatment locations. Additionally or alternatively, the treatment functionality may be more complicated, for example the treatment functionality may allow for the treatment process to be monitored and/or adjusted. The monitoring may be done automatically, for example by processing the captured images in order to identify when treatment of a particular location is completed, or reached a treatment threshold for stopping treatment in the particular location. Additionally or alternatively, the monitoring may be done manually by monitoring images captured, and displayed, in real time and allowing a user to stop and/or adjust the treatment according to the displayed images.

FIG. 13 depicts one illustrative treatment process (1304a), which comprises capturing real time images of the eye using the SLO and OCT imaging system (1306) and loading the images stored in association with the treatment plan (1308). The captured images and images associated with the treatment plan are registered to each other (1310) and the treatment plan displayed (1312). If the treatment should proceed (Yes at 1314), the laser treatment begins (1316) which may include monitoring eye movement in real time using the SLO system to update the treatment locations to account for the eye movement as well as possibly identify unsafe treatment regions in the eye. The images captured in real time may be displayed (1318) along with the progression of the treatment plan (1320). If the treatment is not to proceed (No at 1314) the treatment plan may be edited (1322), which may include for example loading the treatment type planning functionality as described above (1324) in order to edit the treatment plan. Once the treatment plan is edited, it can be approved (1326) and stored with the patient information (1328) before again displaying the plan for approval to proceed (1314).

The above has described a flexible imaging and laser treatment system that can be used to identify and treat numerous different eye conditions. The system may include multiple different treatment lasers that are used to treat the different conditions, or the system may have an interchangeable treatment laser system that allows different treatment laser sources to be used. Regardless, the system can be used to identify ocular conditions, generate treatment plans and carry out the treatment in a single session, or multiple sessions. The system can be used to treat a wide range of conditions including for example, age-related macular degeneration (AMD), vitreomacular traction, and diabetic retinopathy, among other conditions.

Previous treatment of vitreomacular traction has severed the traction causing vitreous humor strands with focused radiation from an Nd:YAG laser. The severing may be affected by the pressure wave of photo disruptions which are caused by the high pulse energies in the mJ range at pulse durations of a few ns. These pressure waves may also damage the surrounding tissue, making the use of this method impossible in immediate proximity of the retina.

The imaging and laser deliver system may be configured with a treatment laser capable of making precise incision in transparent media without damaging the surrounding tissue, allowing the system to be used in treating vitreomacular traction. The system may be configured with a treatment laser that is an ultrashort pulse laser with pulse widths in the range of <300 fs, pulse energies in the range of 1-2 µJ, and pulse repetition rates of approximately >500 kHz. The diameter of the laser beam in the eye pupil maybe preferably between 2 and 4 mm. The beam divergence can be varied in order to realize a shift of the focal position in axial direction (z-scan or z-axis as described above). The treatment laser system is coupled to a scanner/targeting system which allows the spatial variation of the focus in three dimensions (x, y, and z). The eye to be treated may be mechanically, and optically, coupled via a contact glass which can be suctioned to the cornea or the sclera of the eye using a vacuum. In this case, the laser radiation is coupled in the eye via the contact glass. A focusing optics with a numerical aperture of approximately 0.1 (0.05-0.2) may be provided.

In addition to the treatment laser scanner optical system, the device furthermore includes a navigation system which comprises a confocal optical detection (SLO) and an optical coherence tomography (OCT). A machine learning (ML) algorithm, or other techniques including manual techniques, may detect and triangulate the retina segment that is under traction and may also detect the region of the vitreous strands that cause traction of the retina. The ML algorithm may then provide a suggested treatment procedure that will result in the smallest amount of cutting, or other characteristics such as greater amount of cutting but safer cutting locations, required in order to release the tension on the retina. The particular shape of the cutting path may vary depending upon factors of each patient, however the shape of the cut used for severing the connection of the vitreous cortex to the retina may have a general convex shape surface that wraps around the traction region. The specific shape of the cuts may be determined by the ML algorithm, which may consider what location and path of treatment will result in the best outcome for the patient. The ML algorithm may estimate optimal laser parameters as well.

Figure 14:
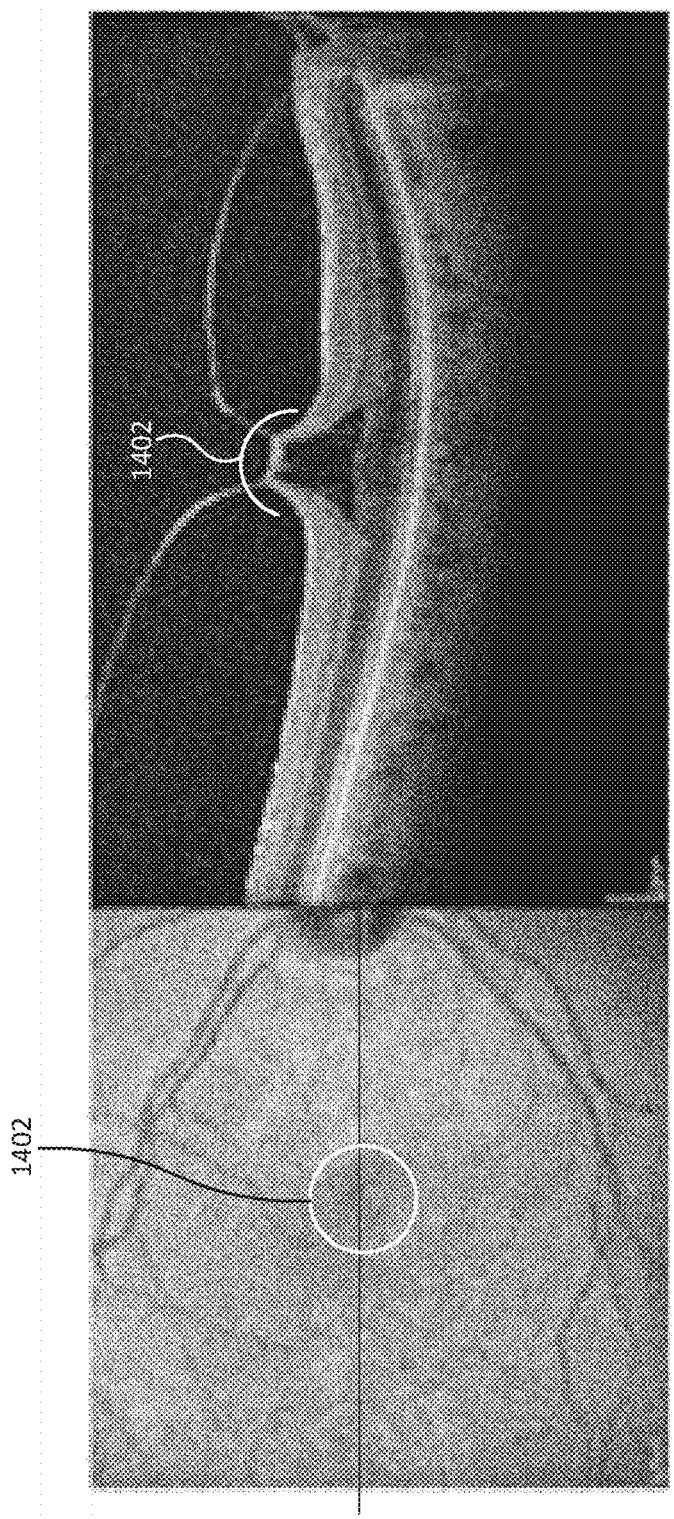
FIG. 14 depicts a convex shape surface on a fundus image and OCT image of a patient with vitreomacular traction

FIG. 14 depicts a convex shape surface on a fundus image and OCT image of a patient with vitreomacular traction. The fundus image and the corresponding OCT image depict a patient with vitreomacular traction. The convex shape surface 1402 may be used to sever the vitreous strands. The convex shape surface 1402 describes the pathway of therapeutic laser for the purpose of cutting/ablating the vitreous strands, in order to release it from the retina, and treat macular traction.

The system as described has a control system which can provide control data to the treatment laser and the scanner system. When control data are generated, it is taken into account that in case of incisions in the vitreous humor, the radiation exposure of the retina does not exceed the known thresholds for damage to surrounding tissue. For this purpose, the energy and power density may be calculated locally on the retina using an optical model, and the temporal and spatial sequence of the applied pulses may be varied during the treatment phase so that the radiation exposure for each location on the retina is below the damage threshold. In addition to simply setting the laser parameters to be below an expected damage threshold, it is possible to use the A-scan data from the OCT images in order to identify a formation of a bubble in the treatment area which may be indicative of tissue being damaged as so the treatment to the region should be stopped or paused. That is, the system may stop the irradiation of each treatment spot based on the data from the OCT interferometer.

It may be advantageous to distribute the incisions relatively evenly in the volume of the vitreous humor, wherein a safety distance to the retina must be observed. The system may provide functionality which detects at least the posterior boundary layers of the crystalline lens and the retina based on the data from the OCT interferometer. The functionality may provide for the identification of the vitreous body strand structures which cause the tensile loads and the reduction of the tensile forces using appropriate relief incisions.

During the planning phase for treatment of VMT, patient images may be imported into the system and the doctor or specialist may choose to either manually mark the treatment pathway, or approve a computer-aided treatment pathway that may be generated automatically. The patient information and treatment plan or pathway may then be stored for future execution.

During the execution phase, the patient may in front of the imaging and laser delivery device, and the contact lens is contacted to the eye. The SLO imaging obtains a raster scan of the patient's retina. The SLO raster scan is matched with the image, or images, associated with the previously generated treatment pathway plan. The system translates the treatment coordinates, such that they correspond with the device imaging orientation. The SLO imaging system continues to image the patient's retina in order to continuously track the movement of the patient's eye. When the system coordinates are locked, and it is safe to perform treatment, the doctor or specialist may provide an indication to proceed, such as pressing and/or holding a button. During the procedure a live stream of OCT and SLO images may be displayed in order to track the progress of the treatment. The OCT and SLO images captured during the treatment may be stored for future reference, possibly for further patient treatment or evaluation of the treatment. Additionally the stored images may also be used a training corpus for training of machine learning algorithms of the system for identifying different conditions.

In addition to treating vitreomacular traction as described above, the system may also be used in treating diabetic retinopathy. Diabetic retinopathy results in damage to the retina due to complications of diabetes. If left untreated, diabetic retinopathy can eventually lead to blindness. Diabetic retinopathy typically results from microvascular retinal changes. For example, diabetic induced effects may damage tissue of the eye, which may change the formation of the blood-retinal barrier and make the retinal blood vessels become more permeable. In treating such conditions, one or more light beams may be directed into the eye and/or onto retinal tissue to cause photocoagulation of the tissue so as to finely cauterize ocular blood vessels and/or prevent blood vessel growth to induce various therapeutic benefits.

In providing laser photocoagulation treatments, however, it is important to avoid damaging sensitive tissue of the eye, such as the fovea, macula, etc. In certain instances, it may be desired to treat tissue close to these areas while ensuring that damage to such areas is avoided. The current system may be used to accurately target and deliver the treatment laser to the desired locations. In addition to the accurate targeting along the x, y and z axes the system may also use the real-time imaging of the SLO and OCT imaging systems to ensure the laser treatment does not damage surrounding tissue. The laser beam of the treatment laser can be targeted as a pattern of geometric shapes to be directed to deliver the treatment. The geometric pattern can be either manually created by the doctor, or automatically generated by the computing device based on captured images.

The pattern of geometric shapes may be defined on the retinal tissue of the eye by (i.e. on the image of the SLO and OCT). The pattern of geometric shapes may include: a grid having a plurality of squares, a grid having a plurality of rectangles, a semicircle pattern, a pattern of circles, a hexagonal pattern, etc. The treatment pattern may include or define a grid having a plurality of rows and columns. The grid may include an M×N array of squares or rectangles arranged in a linear or semicircular pattern. Delivering the treatment laser treatment causes photocoagulation of the retinal tissue. The treatment beam may be delivered in a series of pulses of sufficiently short duration so as to avoid inducing traditional photocoagulation of the retinal tissue while inducing photo activation of a therapeutic healing response. The planning and treatment phases for treating diabetic retinopathy may be similar to the planning and treatment phases described above for vitreo-retinal traction although the treatment locations and laser parameters for the treatment locations may be different.

Other ocular conditions that may be treated in a similar manner by accurately targeting a treatment laser in the x, y, z directions. For example age-related macular degeneration (AMD) may be treated by targeting drusen locations for radiation by the treatment laser. Other ocular conditions may be treated in a similar manner. Additionally, the combination of the real time imaging and treatment may be used to correct conditions that may require changes to the treatment plan as treatment occurs. Tears, detachments, and holes may be treated using the treatment laser; however, as the treatment occurs the position for further treatments may move. For example, laser treatment of a tear may cause the remaining portions of the tear to move, the real time imaging systems may be used to determine the new treatment location by identifying the new locations of the tear.

As described above, the imaging and therapeutic laser delivery system may be used in the treatment of one or more eye conditions, including diabetic retinopathy, age-related macular degeneration, vitreomacular traction, tears, detachments, holes, glaucoma, and vein occlusion.

It will be appreciated by one of ordinary skill in the art that the system and components shown in FIGS. 1-14 may include components not shown in the drawings. For simplicity and clarity of the illustration, elements in the figures are not necessarily to scale, are only schematic and are non-limiting of the elements structures. It will be apparent to persons skilled in the art that a number of variations and modifications can be made without departing from the scope of the invention as defined in the claims.

Although certain components and steps have been described, it is contemplated that individually described components, as well as steps, may be combined together into fewer components or steps or the steps may be performed sequentially, non-sequentially or concurrently. Further, although described above as occurring in a particular order, one of ordinary skill in the art having regard to the current teachings will appreciate that the particular order of certain steps relative to other steps may be changed. Similarly, individual components or steps may be provided by a plurality of components or steps. One of ordinary skill in the art having regard to the current teachings will appreciate that the components and processes described herein may be provided by various combinations of software, firmware and/or hardware, other than the specific implementations described herein as illustrative examples.

The techniques of various embodiments may be implemented using software, hardware and/or a combination of software and hardware. Various embodiments are directed to apparatus, e.g. a node which may be used in a communications system or data storage system. Various embodiments are also directed to non-transitory machine, e.g., computer, readable medium: e.g., ROM, RAM, CDs, hard discs, etc., which include machine readable instructions for controlling a machine, e.g., processor to implement one, more or all of the steps of the described method or methods.

Some embodiments are directed to a computer program product comprising a computer-readable medium comprising code for causing a computer, or multiple computers, to implement various functions, steps, acts and/or operations, e.g. one or more or all of the steps described above. Depending on the embodiment, the computer program product can, and sometimes does, include different code for each step to be performed. Thus, the computer program product may, and sometimes does, include code for each individual step of a method, e.g., a method of operating a communications device, e.g., a wireless terminal or node. The code may be in the form of machine, e.g., computer, executable instructions stored on a computer-readable medium such as a RAM (Random Access Memory), ROM (Read Only Memory) or other type of storage device. In addition to being directed to a computer program product, some embodiments are directed to a processor configured to implement one or more of the various functions, steps, acts and/or operations of one or more methods described above. Accordingly, some embodiments are directed to a processor, e.g., CPU, configured to implement some or all of the steps of the method(s) described herein. The processor may be for use in, e.g., a communications device or other device described in the present application.

Numerous additional variations on the methods and apparatus of the various embodiments described above will be apparent to those skilled in the art in view of the above description. Such variations are to be considered within the scope.

What is claimed is:

1. An imaging and laser delivery system for treatment of an eye condition, the system comprising:
   a scanning laser ophthalmoscopy (SLO) system comprising an SLO detector and an SLO light source, wherein the SLO light source is configured to generate light for passing from the SLO light source through an SLO optical pathway for SLO imaging;
   an optical coherence tomography (OCT) system comprising an OCT detector and an OCT light source, wherein the OCT light source is configured to generate light for passing from the OCT light source through an OCT optical pathway for OCT imaging;

a treatment laser comprising a femtosecond laser configured to generate light from the treatment laser for passing through a treatment optical pathway;

an objective lens configured to focus light from the SLO optical pathway, the OCT optical pathway and the treatment optical pathway onto a portion of an eye being treated for the eye condition;

a splitter, wherein the splitter is configured to direct light from the SLO light source and reflected from the eye back to the SLO optical pathway, and wherein the splitter is further configured to direct light from the OCT light source and reflected from the eye back to the OCT optical pathway; and a device controller for controlling operation of the treatment laser and components of the SLO optical pathway, the OCT optical pathway and the treatment optical pathway, wherein a focus of the treatment laser is adjustable by the device controller to allow for spatial variation of the focus of the treatment laser in three-dimensional space within the eye; and wherein the system includes a machine learning algorithm configured to generate, based on images from the SLO system or the OCT system, one or more parameters for modifying a treatment plan to control the treatment laser for delivering one or more light beams to the eye, wherein the one or more parameters comprise at least one of: a shape of a cutting path of the treatment laser, a path of treatment with the treatment laser, a location of treatment with the treatment laser, and optimal laser parameters for the treatment laser.

2. The imaging and laser delivery system of claim 1, wherein a reference pathway of the OCT optical pathway comprises an adjustable thickness material to compensate for dispersion within the eye.

3. The imaging and laser delivery system of claim 2, wherein the treatment optical pathway comprises at least one of adaptive optics, prism pair, grating pair, dielectric mirror coatings, and optical fiber for pre-compensating a treatment laser pulse based on the thickness of the adjustable thickness material in the reference pathway of the OCT optical pathway.

4. The imaging and laser delivery system of claim 1, further comprising:
an alignment system for aligning the treatment laser to the OCT optical pathway.

5. The imaging and laser delivery system of claim 4, wherein the alignment system comprise a coarse alignment section and a fine alignment section.

6. The imaging and laser delivery system of claim 5, wherein the coarse alignment section comprise a pair of CMOS sensors arranged at respective ends of different length optical paths of a coarse alignment beam split from the treatment laser, and wherein the fine alignment section comprises a pair of quadrature photodiodes (QPD) arranged at respective ends of different length optical paths of a fine alignment beam split from the treatment laser.

7. The imaging and laser delivery system of claim 4, wherein the alignment system comprises positioning optics for controllably adjusting the alignment of the treatment laser.

8. The imaging and laser delivery system of claim 1, further comprising a pilot laser passing through at least a portion of the treatment optical pathway, the pilot laser has a pilot wavelength that can be detected by at least one of the SLO detector and the OCT detector and used to align the treatment laser with at least one of the SLO imaging and the OCT imaging.

9. The imaging and laser delivery system of claim 8, further comprising a beam splitter for directing a portion of the pilot laser returning from the eye to a pilot sensor for detecting the pilot laser, wherein the pilot sensor is used to generate an image of the eye that can be registered to an SLO image.

10. The imaging and laser delivery system of claim 1, further comprising a beam splitter for directing a portion of the treatment laser returning from the eye to a treatment sensor for detecting the treatment laser, wherein the treatment sensor is used to generate an image of the eye that can be registered to an SLO image.

11. The imaging and laser delivery system of claim 1, wherein the eye condition comprises one or more of diabetic retinopathy, age-related macular degeneration, vitreomacular traction, tears, detachments and holes, glaucoma, vein occlusion, and vitreous strands.

12. The imaging and laser delivery system of claim 1, wherein the system further comprises a dispersion compensation component, and wherein the device controller is further configured to control operation of the dispersion compensation component.

13. The imaging and laser delivery system of claim 12, wherein the dispersion compensation component is adjustable by the device controller to place an image captured by the OCT detector into sharp focus.

14. The imaging and laser delivery system of claim 12, wherein the device controller is further configured to stop the treatment laser when tracking of the eye's movement is unreliable.

15. The imaging and laser delivery system of claim 12, wherein the device controller is further configured to register the treatment laser, SLO system, and OCT system against a treatment plan to focus the treatment laser in three-dimensional space within the eye.

16. A laser imaging and delivery system for treatment of an eye condition comprising:
an imaging and laser delivery system according to claim 1; and
a computing device in communication with the controller of the imaging and laser delivery device, the computing device for controlling operation of the imaging and laser delivery device and providing a graphical user interface to a user of the imaging and laser delivery system.

17. The imaging and laser delivery system of claim 16, wherein the computing device is configured to:
capture an SLO image and an OCT image;
identify corresponding features in the SLO image and the OCT image; and
register the captured SLO and OCT images based on the corresponding features.

18. The imaging and laser delivery system of claim 16, wherein the computing device is configured to:
capture SLO images and OCT images;
register the captured SLO images and OCT images to planning images of a treatment plan for treating the eye condition; and
controlling the treatment laser according to the treatment plan.

19. The imaging and laser delivery system of claim 16, wherein the computing device is further configured to:
track eye movement using the captured SLO images; and control the treatment laser according to the treatment plan and the tracked eye movement.

20. The imaging and laser delivery system of claim 16, wherein the computing device is further configured to:
identify unsafe regions for laser treatment within the eye; and
stop the treatment laser if treatment will occur within the unsafe regions.

21. The imaging and laser delivery system of claim 16, wherein the computing device is further configured to:
generate a graphical user interface (GUI) displaying the SLO images and OCT images, wherein the GUI is used to generate the treatment plan and display progress of the treatment plan during treatment.

\* \* \* \* \*